(12) United States Patent
Nikolski et al.

(10) Patent No.: US 12,186,572 B2
(45) Date of Patent: Jan. 7, 2025

(54) IMPLANTABLE MEDICAL LEAD WITH SHIELD

(71) Applicant: Medtronic, Inc., Minneapolis, MN (US)

(72) Inventors: Vladimir P. Nikolski, Blaine, MN (US); Mark T. Marshall, Cape Coral, FL (US); Jeffrey D. Wilkinson, Vadnais Heights, MN (US); Amy E. Thompson-Nauman, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 48 days.

(21) Appl. No.: 17/185,784

(22) Filed: Feb. 25, 2021

(65) Prior Publication Data
US 2021/0268297 A1 Sep. 2, 2021

Related U.S. Application Data

(60) Provisional application No. 62/982,790, filed on Feb. 28, 2020.

(51) Int. Cl.
*A61N 1/36* (2006.01)
*A61N 1/375* (2006.01)
(Continued)

(52) U.S. Cl.
CPC ..... *A61N 1/39622* (2017.08); *A61N 1/36182* (2013.01); *A61N 1/37512* (2017.08); *A61N 1/0504* (2013.01)

(58) Field of Classification Search
CPC ............ A61N 1/39622; A61N 1/36182; A61N 1/37512; A61N 1/0504; A61N 1/3622; A61N 1/362; A61N 1/3918
See application file for complete search history.

(56) References Cited

U.S. PATENT DOCUMENTS

| 4,257,424 A | 3/1981 | Cartmell |
| 4,524,775 A | 6/1985 | Rasmussen |

(Continued)

FOREIGN PATENT DOCUMENTS

| WO | 2019197684 A1 | 10/2019 |

OTHER PUBLICATIONS

International Search Report and Written Opinion of International Application No. PCT/US2021/020041, mailed Jun. 22, 2021, 10 pp.
(Continued)

*Primary Examiner* — Eugene T Wu
(74) *Attorney, Agent, or Firm* — Shumaker & Sieffert, P.A.

(57) ABSTRACT

This disclosure describes implantable medical leads and medical device systems utilizing the leads. In some examples, an implantable medical lead comprises a first defibrillation electrode and a second defibrillation electrode, the first and second defibrillation electrodes configured to deliver anti-tachyarrhythmia shocks, and a pace electrode disposed between the first defibrillation electrode and the second defibrillation electrode, the pace electrode configured to deliver a pacing pulse that generates an electric field proximate to the pace electrode. The implantable medical lead further comprises a shield disposed between the first defibrillation electrode and the second defibrillation electrode and over a portion of an outer surface of the pace electrode, wherein the shield is configured to impede the electric field in a direction from the pace electrode away from a heart.

19 Claims, 14 Drawing Sheets

(51) Int. Cl.
*A61N 1/39* (2006.01)
*A61N 1/05* (2006.01)

(56) References Cited

U.S. PATENT DOCUMENTS

| | | | |
|---|---|---|---|
| 4,870,969 | A | 10/1989 | Swartz |
| 5,477,855 | A | 12/1995 | Schindler et al. |
| 5,897,554 | A | 4/1999 | Chia et al. |
| 6,330,481 | B1 | 12/2001 | Van Wijk et al. |
| 7,862,563 | B1 | 1/2011 | Cosman et al. |
| 8,788,064 | B2 | 7/2014 | Mercanzini et al. |
| 10,143,844 | B2 | 12/2018 | Baru et al. |
| 10,531,893 | B2 | 1/2020 | Seifert et al. |
| 2002/0035381 | A1 | 3/2002 | Bardy et al. |
| 2004/0215308 | A1 | 10/2004 | Bardy et al. |
| 2007/0239244 | A1 | 10/2007 | Morgan et al. |
| 2008/0071178 | A1* | 3/2008 | Greenland ......... A61N 1/36564 600/486 |
| 2010/0036466 | A1 | 2/2010 | Min et al. |
| 2012/0029335 | A1 | 2/2012 | Sudam et al. |
| 2012/0035616 | A1 | 2/2012 | Olsen et al. |
| 2013/0013045 | A1* | 1/2013 | Soltis ................ A61N 1/0558 607/118 |
| 2014/0330287 | A1 | 11/2014 | Thompson-Nauman et al. |
| 2016/0158567 | A1* | 6/2016 | Marshall ............. A61N 1/0504 607/116 |
| 2017/0354365 | A1 | 12/2017 | Zhou |
| 2018/0036527 | A1 | 2/2018 | Reddy et al. |
| 2018/0133458 | A1* | 5/2018 | Foster ................ A61N 1/0504 |
| 2019/0126051 | A1 | 5/2019 | Strommer et al. |

OTHER PUBLICATIONS

International Preliminary Report on Patentability from International Application No. PCT/US2021/020041 dated Sep. 9, 2022, 8 pp.
Communication pursuant to Article 94(3) EPC from counterpart European Application No. 21714467.4 dated Feb. 16, 2024, 6 pp.
Response to Communication pursuant to Article 94(3) EPC dated Feb. 16, 2024, from counterpart European Application No. 21714467.4 filed Jun. 4, 2024, 8 pp.

* cited by examiner

IMPLANTABLE MEDICAL LEAD WITH SHIELD

This application claims the benefit of U.S. Provisional Application Ser. No. 62/982,790, filed Feb. 28, 2020, the entire content of which is incorporated herein by reference.

TECHNICAL FIELD

The present application relates to implantable medical leads and, more particularly, implantable medical leads with one or more structures to reduce the likelihood of stimulation of unintended tissue.

BACKGROUND

Malignant tachyarrhythmia, for example, ventricular fibrillation (VF), is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. As a consequence, sudden cardiac death (SCD) may result in a matter of minutes.

In patients with a high risk of VF, the use of implantable systems, such as an implantable cardioverter defibrillator (ICD) system has been shown to be beneficial at preventing SCD. Implantable systems, such as pacemakers with or without cardioversion or defibrillation capabilities, may also treat other cardiac dysfunction, such as bradycardia and heart failure. Such implantable systems may include electrical devices configured to deliver therapy via electrodes. Therapy may include shocks and/or anti-tachycardia pacing (ATP). The implantable systems may also be configured to deliver cardiac pacing to, for example, treat bradyarrhythmia or for cardiac resynchronization therapy (CRT).

The implantable system may include one or more implantable medical leads. A distal portion of an implantable medical lead may include one or more electrodes, and may be positioned at a target location within the patient for delivery of electrical therapy and/or electrical sensing via the electrodes. A proximal end of the lead may be coupled to the implantable system. The implantable system may also include one or more housing electrodes, which are sometimes referred to as can electrodes, for delivery of therapy and/or sensing.

Owing to the inherent surgical risks in attaching and replacing implantable medical leads directly within or on the heart, subcutaneous implantable systems have been devised, in which the implantable system and leads are located subcutaneously outside of the thorax. It has also been proposed that the distal portion of a lead of an implantable system may be implanted within the thorax, but not in contact with the heart, e.g., substernally. Additionally, it has been proposed to implant the distal portion of a lead of an implantable system within an extracardiac vessel that is within the thorax, such as the internal thoracic vein (ITV), the intercostal veins, the superior epigastric vein, or the azygos, hemiazygos, and accessory hemiazygos veins.

Implantable medical leads are also used to deliver therapies to tissues other than the heart. Implantable medical leads may be used to position one or more electrodes within or near target nerves, muscles, or organs to deliver electrical stimulation to such tissues. As examples, implantable medical leads may be positioned in the epidural space to deliver spinal cord stimulation, or proximate to other nerves, such as pelvic nerves or renal nerves, to deliver neurostimulation to the nerves.

SUMMARY

Relative to electrodes on or within the heart, delivery of pacing pulses using electrodes of extravascular leads may require higher energy levels to capture the heart. Furthermore, conventional pace electrodes placed extravascularly may direct a significant portion of the electrical field produced by a pacing pulse away from the heart. The electrical field directed away from the heart may stimulate extracardiac tissue, such as the phrenic nerve, nerve endings in the intercostal regions, or other sensory or motor nerves. These issues may similarly occur when electrodes are implanted within extracardiac vessels within the thorax, such as the ITV, the intercostal veins, the superior epigastric vein, or the azygos, hemiazygos, and accessory hemiazygos veins, or when electrodes are implanted in other extracardiac locations.

This disclosure describes implantable medical leads and implantable systems, such as ICD systems, utilizing the leads. More particularly, this disclosure describes implantable medical leads that include a shield configured to impede the electric field from a pacing pulse, e.g., block or reduce the electric field, in a direction from the pace electrode, away from the heart, e.g., an anterior direction. In this manner, the shield may reduce the likelihood that pacing pulses delivered via the pace electrode stimulate extracardiac tissue, such as sensory or motor nerves, which may reduce pain or other sensations associated with capture of such tissue. Furthermore, the shield may direct the electrical field toward the heart, allowing lower energy level pacing pulses to capture the heart than may be required without the shield. Lower energy pacing pulses may also reduce the likelihood that pacing pulses delivered via the pace electrode stimulate extracardiac tissue, and may result is less consumption of the power source of the ICD and, consequently, longer service life for the ICD.

Although described herein primarily in the context of ICD systems, various aspects of the techniques of this disclosure may be applied to implantable systems other than ICD systems, including, but not limited to, bradycardia or CRT pacemaker systems. Accordingly, implantable medical leads having one or more shields may be used in contexts other than that of ICD systems, both cardiac and non-cardiac. As one example, implantable medical leads that have a shield over a portion of a surface of an electrode may be used with an extracardiac pacemaker system without defibrillation capabilities. As another example, implantable medical leads that have a shield over a portion of a surface of an electrode may impede an electrical field resulting from delivery of neurostimulation from the electrode in a direction away from a target nerve. In this manner, the shield may direct the neurostimulation to intended tissue, and reduce the likelihood that the neurostimulation stimulates unintended tissues.

In one example, an implantable medical lead comprises a first defibrillation electrode and a second defibrillation electrode, the first and second defibrillation electrodes configured to deliver anti tachyarrhythmia shocks, and a pace electrode disposed between the first defibrillation electrode and the second defibrillation electrode, the pace electrode configured to deliver a pacing pulse that generates an electric field proximate to the pace electrode. The implantable medical lead further comprises a shield disposed between the first defibrillation electrode and the second defibrillation electrode, over a portion of an outer surface of the pace electrode, and extending laterally away from the pace electrode, wherein the shield is configured to impede the electric field in a direction from the pace electrode away from a heart.

In another example, an implantable cardioverter-defibrillator (ICD) system comprises the implantable medical lead as described above and an ICD configured to deliver the pacing pulse via the pace electrode.

In another example, a method of implanting an implantable medical lead as described above comprises advancing the implantable medical lead to a location within the patient, and rotationally orienting the distal portion of implantable medical lead such that the shield is positioned opposite a heart relative to the pace electrode.

In another example, a method of manufacturing an implantable medical lead as described above comprises attaching the shield to the surface of the pace electrode, and subsequently assembling the shield and the pace electrode on the implantable medical lead.

This summary is intended to provide an overview of the subject matter described in this disclosure. It is not intended to provide an exclusive or exhaustive explanation of the systems, devices, and methods described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

As used herein, relational terms, such as "first" and "second," "over" and "under," "front" and "rear," and the like, may be used solely to distinguish one entity or element from another entity or element without necessarily requiring or implying any physical or logical relationship or order between such entities or elements.

Figure 1A:
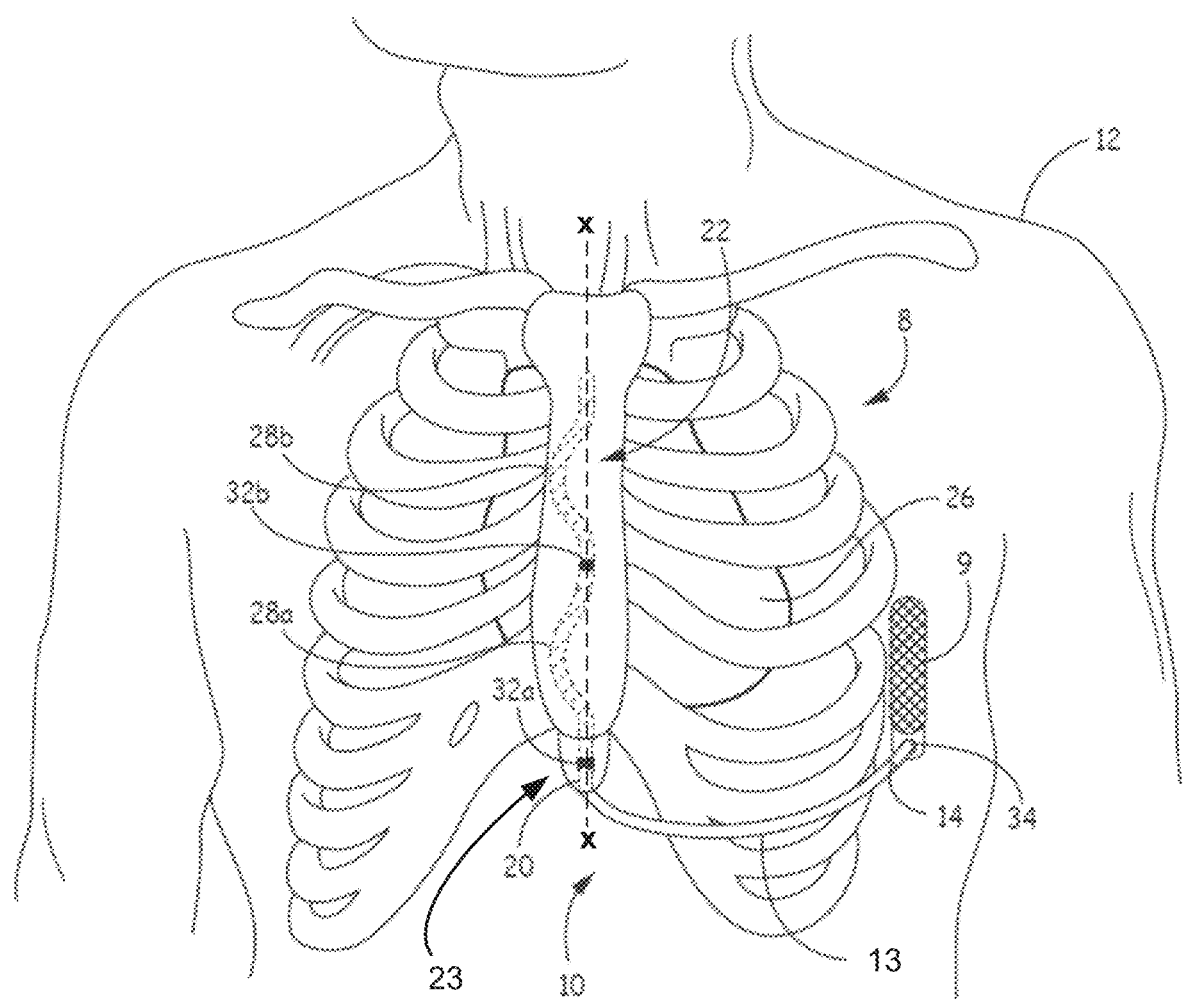
FIG. 1A is a front view of a patient implanted with the extracardiovascular ICD system implanted intra-thoracically.
Figure 1B:
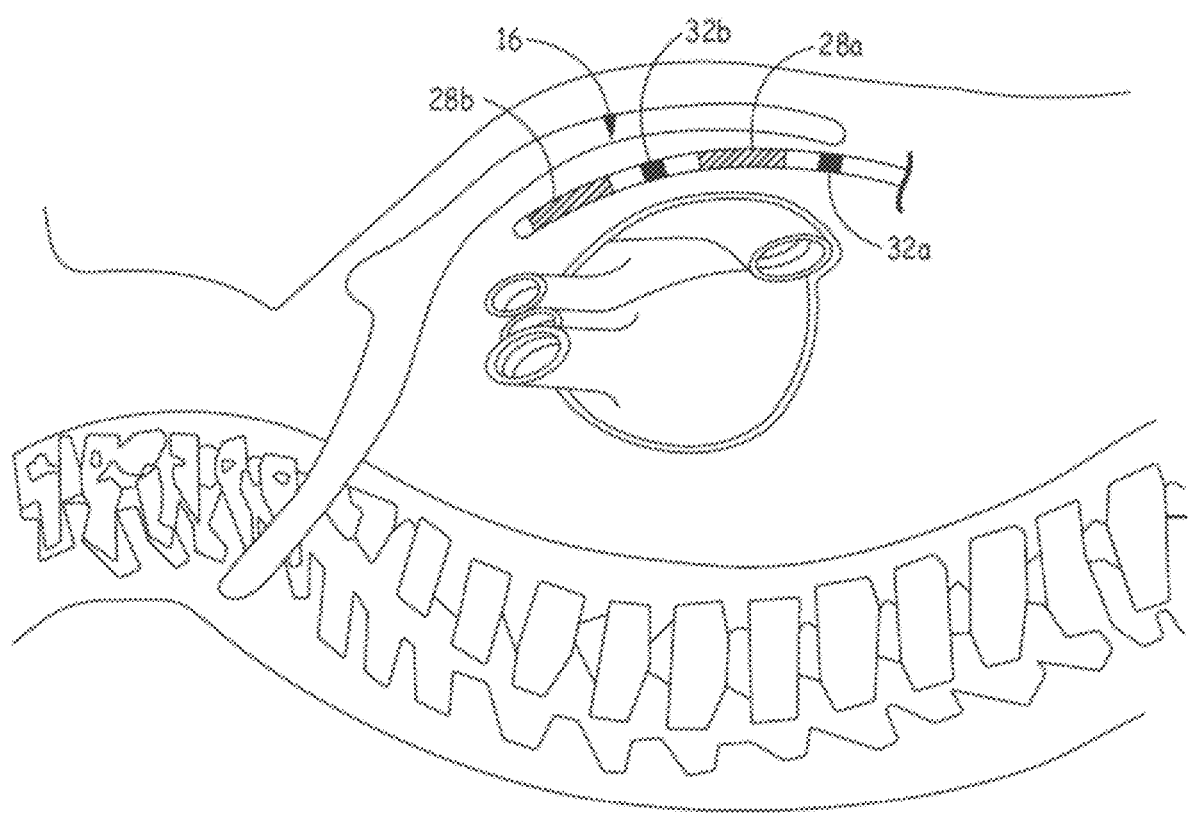
FIG. 1B is a side view of the patient implanted with the extracardiovascular ICD system implanted intra-thoracically.
Figure 1C:
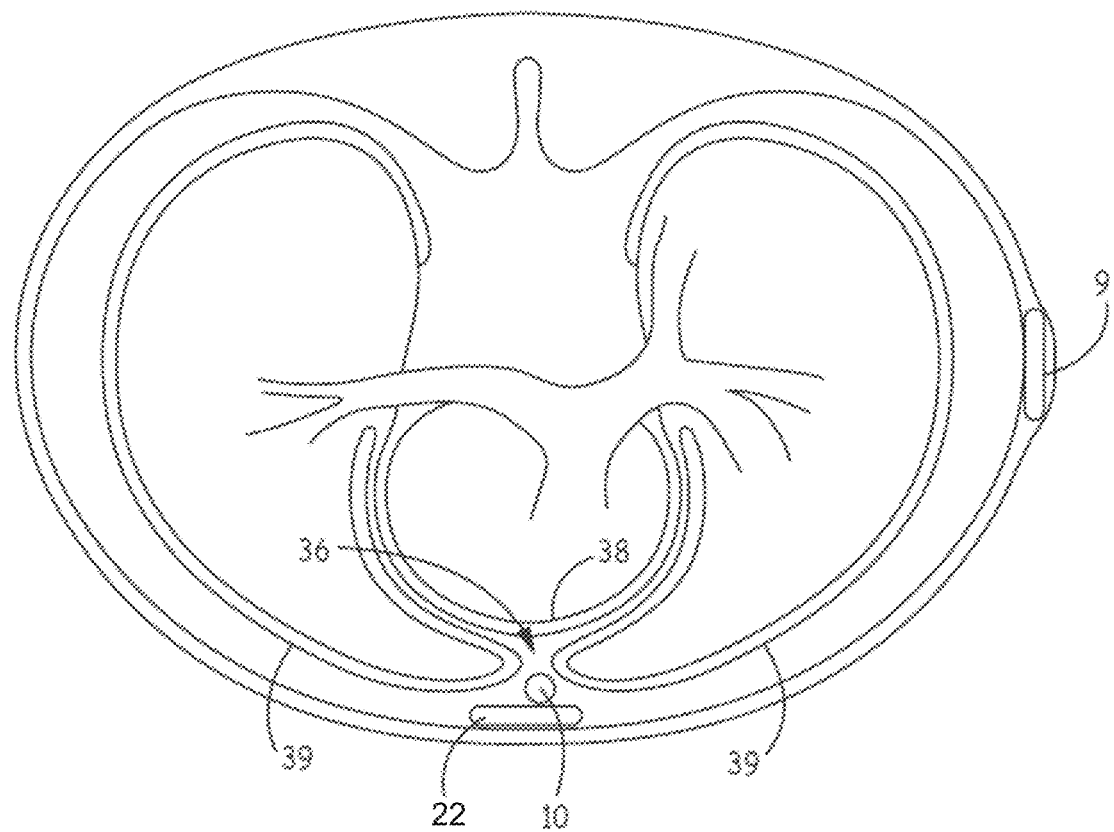
FIG. 1C is a transverse view of the patient implanted with the extracardiovascular ICD system implanted intra-thoracically.

Referring now to the drawings in which like reference designators refer to like elements, there is shown in FIGS. 1A-C conceptual diagrams illustrating various views of an example extracardiovascular implantable cardioverter-defibrillator (ICD) system 8. ICD system 8 includes an ICD 9 connected to an implantable medical lead 10. FIG. 1A is a front view of a patient implanted with extracardiovascular ICD system 8. FIG. 1B is a side view of the patient implanted with extracardiovascular ICD system 8. FIG. 1C is a transverse view of the patient implanted with extracardiovascular ICD system 8.

ICD 9 may include a housing that forms a hermetic seal that protects components of the ICD 9. The housing of ICD 9 may be formed of a conductive material, such as titanium or titanium alloy, which may function as a housing electrode (sometimes referred to as a can electrode). In some embodiments, ICD 9 may be formed to have or may include a plurality of electrodes on the housing. ICD 9 may also include a connector assembly (also referred to as a connector block or header) that includes electrical feedthroughs through which electrical connections are made between conductors of lead 10 and electronic components included within the housing of ICD 9. As will be described in further detail herein, the housing may house one or more processors, memories, transmitters, receivers, sensors, sensing circuitry, therapy circuitry, power sources and other appropriate components. The housing is configured to be implanted in a patient, such patient 12.

ICD 9 is implanted extra-thoracically on the left side of the patient, e.g., under the skin and outside the ribcage (subcutaneously or submuscularly). ICD 9 may, in some instances, be implanted between the left posterior axillary line and the left anterior axillary line of the patient. ICD 9 may, however, be implanted at other extra-thoracic locations on the patient as described later.

Lead 10 may include an elongated lead body 13 having a distal portion 16 sized to be implanted in an extracardiovascular location proximate the heart, e.g., intra-thoracically, as illustrated in FIGS. 1A-C, or extra-thoracically. For example, lead 10 may extend extra-thoracically under the skin and outside the ribcage (e.g., subcutaneously or submuscularly) from ICD 9 toward the center of the torso of the patient, for example, toward the xiphoid process 23 of the patient. At a position proximate xiphoid process 23, the lead body 13 may bend or otherwise turn and extend superiorly. The bend may be pre-formed and/or lead body 13 may be flexible to facilitate bending. In the example illustrated in FIGS. 1A-C, the lead body 13 extends superiorly intra-thoracically underneath the sternum, in a direction substantially parallel to the sternum.

In one example, distal portion 16 of lead 10 may reside in a substernal location such that distal portion 16 of lead 10 extends superior along the posterior side of the sternum substantially within the anterior mediastinum 36. Anterior mediastinum 36 may be viewed as being bounded laterally by pleurae 39, posteriorly by pericardium 38, and anteriorly by the sternum 22. In some instances, the anterior wall of anterior mediastinum 36 may also be formed by the transversus thoracis and one or more costal cartilages. Anterior mediastinum 36 includes a quantity of loose connective tissue (such as areolar tissue), adipose tissue, some lymph vessels, lymph glands, substernal musculature (e.g., transverse thoracic muscle), the thymus gland, branches of the internal thoracic artery, and the ITV.

In another example, lead body 13 may extend superiorly extra-thoracically (instead of intra-thoracically), e.g., either subcutaneously or submuscularly above the ribcage/sternum. Lead 10 may be implanted at other locations, such as over the sternum, offset to the right of the sternum, angled lateral from the proximal or distal end of the sternum, or the like. In other examples, lead 10 may be implanted within an extracardiac vessel within the thorax, such as the ITV, the intercostal veins, the superior epigastric vein, or the azygos, hemiazygos, and accessory hemiazygos veins. In some examples, distal portion 16 of lead 10 may be oriented differently than is illustrated in FIGS. 1A-1C, such as orthogonal or otherwise transverse to sternum 22 and/or inferior to heart 26. In such examples, distal portion 16 of lead 10 may be at least partially within anterior mediastinum 36.

Lead body 13 may have a generally tubular or cylindrical shape and may define a diameter of approximately 3-9 French (Fr). However, lead bodies of less than 3 Fr and more than 9 Fr may also be utilized. In another configuration, lead body 13 may have a flat, ribbon, or paddle shape with solid, woven filament, or metal mesh structure, along at least a portion of the length of the lead body 13. In such an example, the width across lead body 13 may be between 1-3.5 mm. Other lead body designs may be used without departing from the scope of this application.

Lead body 13 may be formed from a non-conductive material, including silicone, polyurethane, fluoropolymers, mixtures thereof, and other appropriate materials, and shaped to form one or more lumens (not shown), however, the techniques are not limited to such constructions. Distal portion 16 may be fabricated to be biased in a desired configuration, or alternatively, may be manipulated by the user into the desired configuration. For example, the distal portion 16 may be composed of a malleable material such that the user can manipulate the distal portion into a desired configuration where it remains until manipulated to a different configuration.

Lead body 13 may include a proximal end 14 and a distal portion 16 which include electrodes configured to deliver electrical energy to the heart or sense electrical signals of the heart. Distal portion 16 may be anchored to a desired position within the patient, for example, substernally or subcutaneously by, for example, suturing distal portion 16 to the patient's musculature, tissue, or bone at the xiphoid process entry site. In some examples, distal portion 16 may be anchored to the patient or through the use of rigid tines, prongs, barbs, clips, screws, and/or other projecting elements or flanges, disks, pliant tines, flaps, porous structures such as a mesh-like elements and metallic or non-metallic scaffolds that facilitate tissue growth for engagement, bioadhesive surfaces, and/or any other non-piercing elements.

Lead body 13 may define a substantially linear portion 20 (FIG. 1A) as it curves or bends near the xiphoid process 23 and extends superiorly. As shown in FIG. 1A, at least a part of distal portion 16 may define an undulating configuration distal to the substantially linear portion 20. In particular, distal portion 16 may define an undulating pattern, e.g., zig-zag, meandering, sinusoidal, serpentine, or other pattern, as it extends toward the distal end of lead 10. In other configurations, lead body 13 may not have a substantially linear portion 20 as it extends superiorly, but instead the undulating configuration may begin immediately after the bend.

Distal portion 16 includes one or more defibrillation electrodes configured to deliver an anti-tachyarrhythmia, e.g., cardioversion/defibrillation, shock to heart 26 of patient 12. In some examples, distal portion 16 includes a plurality of defibrillation electrodes spaced a distance apart from each other along the length of distal portion 16. In the example illustrated by FIGS. 1A-1C, distal portion 16 includes two defibrillation electrodes 28a and 28b (collectively, "defibrillation electrodes 28").

Defibrillation electrodes 28 may be disposed around or within the lead body 13 of the distal portion 16, or alternatively, may be embedded within the wall of the lead body 13. In one configuration, defibrillation electrodes 28 may be coil electrodes formed by a conductor. The conductor may be formed of one or more conductive polymers, ceramics, metal-polymer composites, semiconductors, metals or metal alloys, including but not limited to, one of a combination of the platinum, tantalum, titanium, niobium, zirconium, ruthenium, indium, gold, palladium, iron, zinc, silver, nickel, aluminum, molybdenum, stainless steel, MP35N, carbon, copper, polyaniline, polypyrrole and other polymers. In another configuration, each of defibrillation electrodes 28 may be a flat ribbon electrode, a paddle electrode, a braided or woven electrode, a mesh electrode, a directional electrode, a patch electrode or another type of electrode configured to deliver a cardioversion/defibrillation shock to heart 26 of patient 12.

In one configuration, defibrillation electrodes 28 are spaced approximately 0.25-4.5 cm, and in some instances between 1-3 cm apart from each other. In another configuration, defibrillation electrodes 28 are spaced approximately 0.25-1.5 cm apart from each other. In a further configuration, defibrillation electrodes 28 are spaced approximately 1.5-4.5 cm apart from each other.

In the configuration shown in FIGS. 1A-1C, defibrillation electrodes 28 span a substantial part of distal portion 16. Each of defibrillation electrodes 28 may be between approximately 1-10 cm in length, between approximately 2-6 cm in length, or between approximately 3-5 cm in length. However, lengths of greater than 10 cm and less than 1 cm may be utilized in accordance with the techniques of this disclosure. A total length of defibrillation electrode on distal portion 16, e.g., length of the two defibrillation electrodes 28 combined, may vary depending on a number of variables. In one example, the total length may be between approximately 5-10 cm. However, the defibrillation electrodes 28 may have a total length less than 5 cm and greater than 10 cm in other embodiments. In some instances, defibrillation electrodes 28 may be approximately the same length or, alternatively, different lengths.

Defibrillation electrodes 28 may be electrically connected to one or more conductors, which may be disposed in the body wall of lead body 13 or in one or more insulated lumens (not shown) defined by lead body 13. In an example configuration, each of defibrillation electrodes 28 is connected to a common conductor such that a voltage may be applied simultaneously to all defibrillation electrodes 28 to deliver an anti-tachyarrhythmia shock to heart 26. In other configurations, defibrillation electrodes 28 may be attached to separate conductors such that each defibrillation electrode 28 may apply a voltage independent of the other defibrillation electrodes 28. In this case, ICD 9 or lead 10 may include one or more switches or other mechanisms to electrically connect the defibrillation electrodes together to function as a common polarity electrode such that a voltage may be applied simultaneously to all defibrillation electrodes 28 in addition to being able to independently apply a voltage.

Distal portion 16 may also include one or more pacing and/or sensing electrodes configured to deliver pacing pulses to heart 26 and/or sense electrical activity of heart 26. Such electrodes may be referred to as pacing electrodes, sensing electrodes, or pace/sense electrodes. In the example illustrated by FIGS. 1A-1C, distal portion 16 includes two pace/sense electrodes 32a and 32b (collectively, "pace/sense electrodes 32").

In the illustrated example, pace/sense electrode 32b is positioned between defibrillation electrodes 28, e.g., within a gap between the defibrillation electrodes, and pace/sense electrode 32a is positioned more proximal along distal portion 16 than proximal defibrillation electrode 28a. In some examples, more than one electrode 32 may exist within the gap between defibrillation electrodes 28. In some examples, an electrode 32 is additionally or alternatively located distal of the distalmost defibrillation electrode 28b.

In one example, the distance between the closest defibrillation electrode 28 and electrodes 32 is greater than or equal to approximately 2 mm and less than or equal to approximately 1.5 cm. In another example, electrodes 32 may be spaced apart from the closest one of defibrillation electrodes 28 by greater than or equal to 5 mm and less than or equal to 1 cm. In a further example, electrodes 32 may be spaced apart from the closest one of defibrillation electrodes 28 by greater than or equal to 6 mm and less than or equal to 8 mm.

Electrodes 32 may be configured to deliver low-voltage electrical pulses to the heart or may sense a cardiac electrical activity, e.g., depolarization and repolarization of the heart. As such, electrodes 32 may be referred to herein as pace/sense electrodes 32. In one configuration, electrodes 32 are ring electrodes. However, in other configurations electrodes 32 may be any of a number of different types of electrodes, including ring electrodes, short coil electrodes, paddle electrodes, hemispherical electrodes, or directional electrodes. Each of electrodes 32 may be the same or different types of electrodes as others of electrodes 32. Electrodes 32 may be electrically isolated from an adjacent defibrillation electrode 28 by including an electrically insulating layer of material between electrodes 32 and adjacent defibrillation electrodes 28. Each electrode 32 may have its own separate conductor such that a voltage may be applied to or sensed via each electrode independently from another electrode 32.

Electrodes 28 are referred to as defibrillation electrodes, and electrodes 32 are referred to as pace/sense electrodes, because they may have different physical structures enabling different functionality. Defibrillation electrodes 28 may be larger, e.g., have greater surface area, than pace/sense electrodes 32 and, consequently, may be configured to deliver anti-tachyarrhythmia shocks that have relatively higher voltages than pacing pulses. The relatively smaller size of pace/sense electrodes 32 may provide advantages over defibrillation electrodes for delivering pacing pulses and sensing intrinsic cardiac activity, e.g., lower pacing capture thresholds and/or better sensed signal quality. Nevertheless, a defibrillation electrode 28 may be used to deliver pacing pulses and/or sense electrical activity of the heart, such as in combination with a pace/sense electrode 32.

In the configuration shown in FIGS. 1A-1C, each electrode 32 is substantially aligned along a major longitudinal axis ("x"). In one example, the major longitudinal axis is defined by a portion of elongate body 12, e.g., substantially linear portion 20. In another example, the major longitudinal axis is defined relative to the body of the patient, e.g., along the anterior median line (or midsternal line), one of the sternal lines (or lateral sternal lines), left parasternal line, or other line.

In one configuration, the midpoint of each electrode 32a and 32b is along the major longitudinal axis "x," such that each electrode 32a and 32b is at least disposed at substantially the same horizontal position when the distal portion is implanted within the patient. In some examples, the longitudinal axis "x" may correspond to a caudal-cranial axis of the patient and a horizontal axis orthogonal to the longitudinal axis "x" may correspond to a medial-lateral axis of the patient. In other configurations, the electrodes 32 may be disposed at any longitudinal or horizontal position along the distal portion 16 disposed between, proximal to, or distal to the defibrillation electrodes 28. In the example illustrated in FIG. 1A, electrodes 32 are disposed along the undulating configuration of distal portion 16 at locations that will be closer to heart 26 of patient 12 than defibrillation electrodes 28 (e.g., at a peak of the undulating configuration that is toward the left side of the sternum). As illustrated in FIG. 1A, for example, electrodes 32 are substantially aligned with one another along the left sternal line. In the example illustrated in FIG. 1A, defibrillation electrodes 28 are disposed along peaks of the undulating configuration that extend toward a right side of the sternum away from the heart. This configuration places pace/sense electrodes 32 at locations closer to the heart than electrodes 28, to facilitate cardiac pacing and sensing at relatively lower amplitudes.

In some examples, pace/sense electrodes 32 and the defibrillation electrodes 28 may be disposed in a common plane when distal portion 16 is implanted extracardiovasculalry. In other configurations, the undulating configuration may not be substantially disposed in a common plane. For example, distal portion 16 may define a concavity or a curvature.

Proximal end 14 of lead body 13 may include one or more connectors 34 to electrically couple lead 10 to ICD 9. ICD 9 may also include a connector assembly that includes electrical feedthroughs through which electrical connections are made between the one or more connectors 34 of lead 10 and the electronic components included within the housing. The housing of ICD 9 may house one or more processors, memories, transmitters, receivers, sensors, sensing circuitry, therapy circuitry, power sources (capacitors and batteries), and/or other components. The components of ICD 9 may generate and deliver electrical therapy such as anti-tachycardia pacing, cardioversion or defibrillation shocks, post-shock pacing, and/or bradycardia pacing.

The undulating configuration of distal portion 16 and the inclusion of electrodes 32 between defibrillation electrodes 28 provides a number of therapy vectors for the delivery of electrical therapy to the heart. For example, at least a portion of defibrillation electrodes 28 and one of electrodes 32 may be disposed over the right ventricle, or any chamber of the heart, such that pacing pulses and anti-tachyarrhythmia shocks may be delivered to the heart. The housing of ICD 9 may be charged with or function as a polarity different than the polarity of the one or more defibrillation electrodes 28 and/or electrodes 32 such that electrical energy may be delivered between the housing and the defibrillation electrode 28 and/or electrode 32 to the heart.

Each defibrillation electrode 28 may have the same polarity as every other defibrillation electrode 28 when a voltage is applied to it such that a shock may be delivered from all defibrillation electrodes together. In examples in which defibrillation electrodes 28 are electrically connected to a common conductor within lead body 13, this is the only configuration of defibrillation electrodes 28. However, in other examples, defibrillation electrodes 28 may be coupled to separate conductors within lead body 13 and may therefore each have different polarities such that electrical energy may flow between defibrillation electrodes 28, or between one of defibrillation electrodes 28 and one of pace/sense electrodes 32 or the housing electrode, to provide antitachyarrhythmia shock, pacing therapy, and/or to sense cardiac depolarizations. In this case, defibrillation electrodes 28 may still be electrically coupled together, e.g., via one or more switches within ICD 9, to have the same polarity.

In some examples, distal portion 16 of lead 10 may include one or more shields. The shield or shields may be configured to impede an electric field from delivery of an electrical therapy via an electrode, e.g., from a pacing pulse, in a direction from the electrode away from the heart, e.g., in an anterior direction. In this manner, the shield may reduce the likelihood that the electrical field will stimulate extracardiac tissue, such as sensory or motor nerves. Furthermore, the shield may direct the electrical field toward the heart, allowing lower energy level pacing pulses to capture the heart than may be required without the shield. Lower energy pacing pulses may also reduce the likelihood that pacing pulses delivered via the pace electrode stimulate extracardiac tissue, and may result in less consumption of the power source of ICD 9 and, consequently, longer service life for the ICD. It should be understood that various aspects of the techniques of this disclosure may be applied to implantable systems other than ICD 9, including, but not limited to, bradycardia pacemaker systems. For example, a lead that does not include defibrillation electrodes may include one or more shields and may be used with a pacemaker system without defibrillation capabilities.

Figure 2:
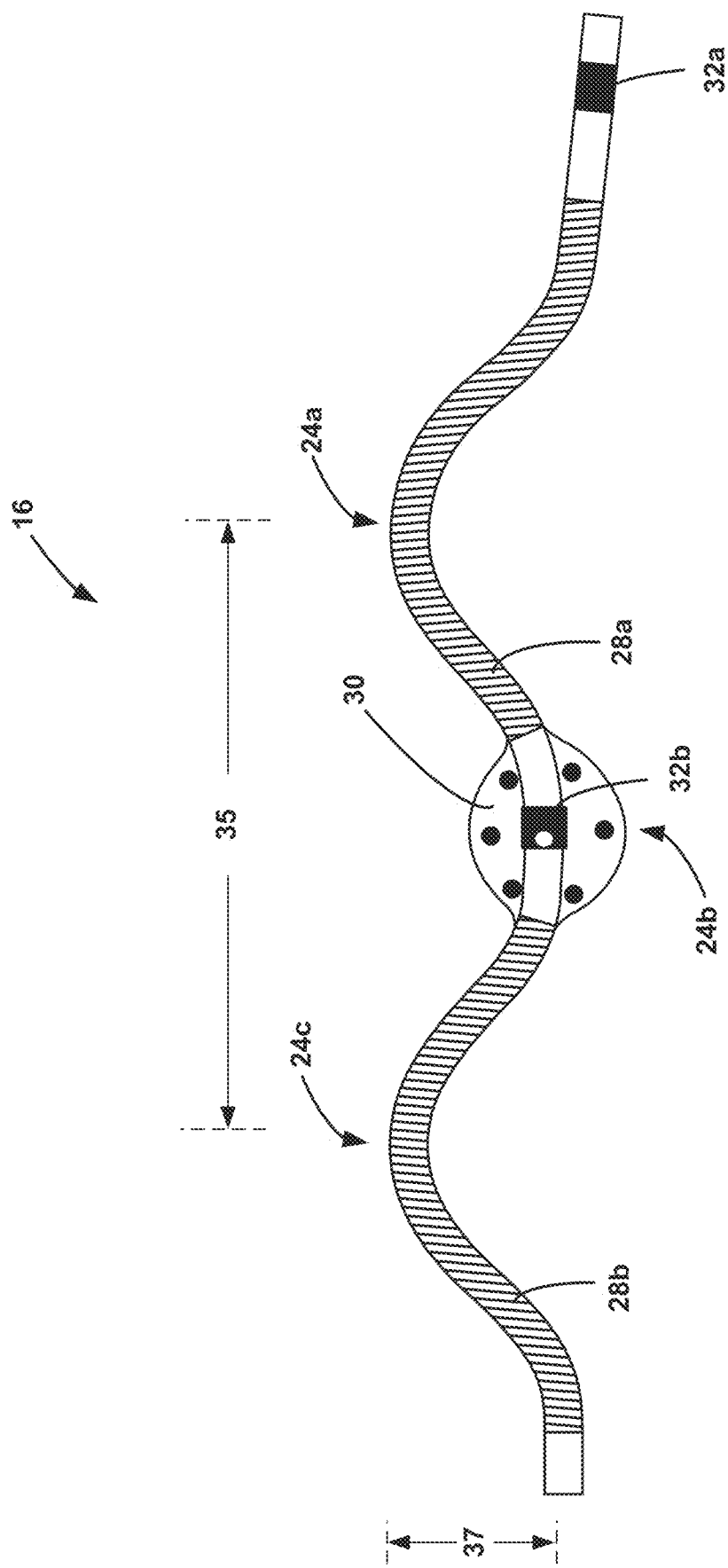
FIG. 2 is a conceptual diagram illustrating a distal portion of an example implantable medical lead comprising a shield.

FIG. 2 is a conceptual diagram illustrating an example configuration of distal portion 16 of implantable medical lead 10. As illustrated in FIG. 2, the undulating configuration of distal portion 16 may include a plurality of peaks along the length of the distal portion. In the example illustrated by FIG. 2, distal portion includes three peaks 24a, 24b, and 24c (collectively, "peaks 24"). Other configurations, however, may include any number of peaks 24.

The undulating configuration may define a peak-to-peak distance 35, which may be variable or constant along the length of distal portion 16. In the configuration illustrated in FIGS. 1-2, the undulating configuration defines a substantially sinusoidal configuration, with a constant peak-to-peak distance 35 of approximately 2.0-5.0 cm. The undulating configuration may also define a peak-to-peak width 37, which may also be variable or constant along the length of the undulating configuration. In the configuration illustrated in FIGS. 1-2, the undulating configuration defines a substantially sinusoidal shape, with a constant peak-to-peak width 37 of approximately 0.5-2.0 cm. However, in other instances, the undulating configuration may define other shapes and/or patterns, e.g., S-shapes, wave shapes, or the like.

Defibrillation electrodes 28 may extend along, e.g., be disposed on or cover, a substantial part of the undulating configuration of distal portion 16, e.g., along at least 80% of the undulating portion. Defibrillation electrodes 28 may extend along more or less than 80% of the undulating configuration. As another example, defibrillation electrodes 28 may extend along at least 90% of the undulating configuration.

Defibrillation electrode 28a extends along a substantial portion of the undulating configuration of distal portion 16 from the proximal end to peak 24b, e.g., along a substantial portion of the first "wave" associated with peak 24a, and the defibrillation electrode segment 28b extends along a substantial portion of the undulating configuration from peak 24b to the distal end of the undulating configuration, e.g., along a substantial portion of the second "wave" associated with peak 24c). In the example illustrated in FIGS. 1-2, a part of the undulating configuration on which defibrillation electrodes 28 are not disposed is a gap between defibrillation electrodes 28a and 28b, on peak 24b, where electrode 32b is disposed.

As illustrated by FIG. 2, distal portion 16 of lead 10 may comprise a shield 30. In the illustrated example, shield 30, like pace/sense electrode 32b, is positioned between defibrillation electrodes 28a and 28b, e.g., on peak 24b of the undulating configuration of distal portion 16. Shield 30 covers or is otherwise disposed over a portion of an outer surface of pace/sense electrode 32b. Shield 30 does not cover an entirety of the outer surface of pace/sense electrode 32b.

Pacing pulses delivered by ICD 9 via pace/sense electrode 32b result in an electrical field proximate the electrode, that "spreads" from the electrode surface toward one or more other electrodes used to deliver the pacing pulse. Shield 30 impedes the electrical field in directions from the electrode toward the shield, and allows the spread in directions from the electrode away from the shield. In this manner, shield 30 is configured to make pace/sense electrode 32b directional.

As illustrated in FIG. 2, shield 30 may extend laterally away from pace/sense electrode 32b, e.g., in a substantially planar manner, such that the dimensions of shield 30 in a plane are greater than those of pace/sense electrode 32b in the plane. In this manner, shield 30 may further (or more effectively) limit the directions, e.g., radial angles, of the spread of the electrical field generated by the pacing pulse from pace/sense electrode 32b. The plane in which shield 30 extends laterally from pace/sense electrode 32b may be the same plane in which peaks 24 of the undulating configuration extend, or a substantially parallel plane. In some examples, such as that illustrated by FIG. 2, shield 30 extends symmetrically from pace/sense electrode 32b, e.g., is symmetrical about a longitudinal axis and/or a transverse axis of pace/sense electrode 32b, such that pace/sense electrode 32b is substantially centered within the outer profile of shield 30 in the plane.

The portion of the outer surface of pace/sense electrode 32b over which shield 30 is positioned may be referred to as an "anterior portion" of the outer surface of pace/sense electrode 32b, since that portion of pace/sense electrode 32b may be more anteriorly positioned within the patient when distal portion 16 of lead 10 is implanted within patient. With shield 30 positioned over an anterior portion of the outer surface of pace/sense electrode 32b, shield 30 may be positioned anteriorly relative to the central longitudinal axis of pace/sense electrode 32b. With shield 30 positioned over an anterior portion of the outer surface of pace/sense electrode 32b, and distal portion 16 implanted within the patient as illustrated in FIGS. 1A-1C, shield 30 may impede the electrical field in directions away from heart 26, referred to as anterior directions.

Shield 30 may be electrically insulative. In some examples, shield 30 comprises a polymer, such as polyurethane. In some examples, shield 30 is configured to be folded or wrapped around pace/sense electrode 32b for delivery via a lumen of an implant tool, and configured to elastically unfold or unwrap to a relaxed condition, e.g., such as the condition shown in FIG. 2, when released from the lumen. In some examples, shield 30 comprises elastic or super-elastic polymer or metallic structures, e.g., Nitinol structures, to encourage the deployment of shield 30, support articulation of shield 30, and/or support shield 30 in the deployed, relaxed configuration. The deployed and/or articulated configuration may be substantially planar, as illustrated in FIG. 2, or may be non-planar. For example, portions of shield 30 spaced further away laterally from pace/sense electrode 32b may be situated more posteriorly than portions closer to the electrode, e.g., in the shape of a cup or bowl.

Such support structures may be partially or fully embedded within a primary material of shield 30, or attached to one or more outer surfaces of shield 30. In some examples, a support structure is located circumferentially around a perimeter of shield 30, e.g., spaced a greatest distance laterally from the shield. However, other support structure locations are possible. For example, one or more support structures may extend in radial or lateral direction from the electrode, e.g., from near electrode to near a periphery of the shield.

Figure 3A:
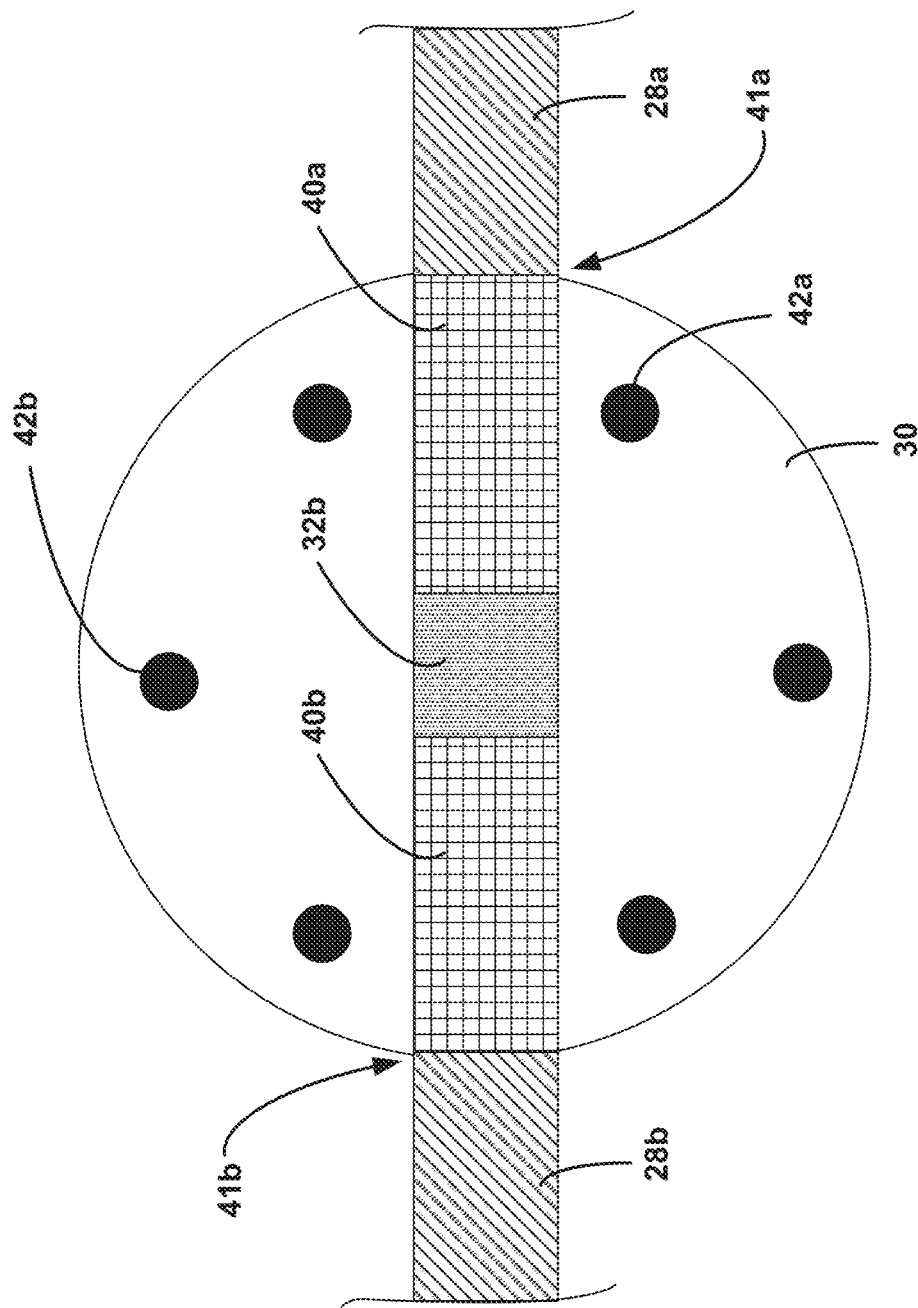
FIGS. 3A-3C are conceptual diagrams illustrating views of an example shield of an implantable medical lead.
Figure 3B:
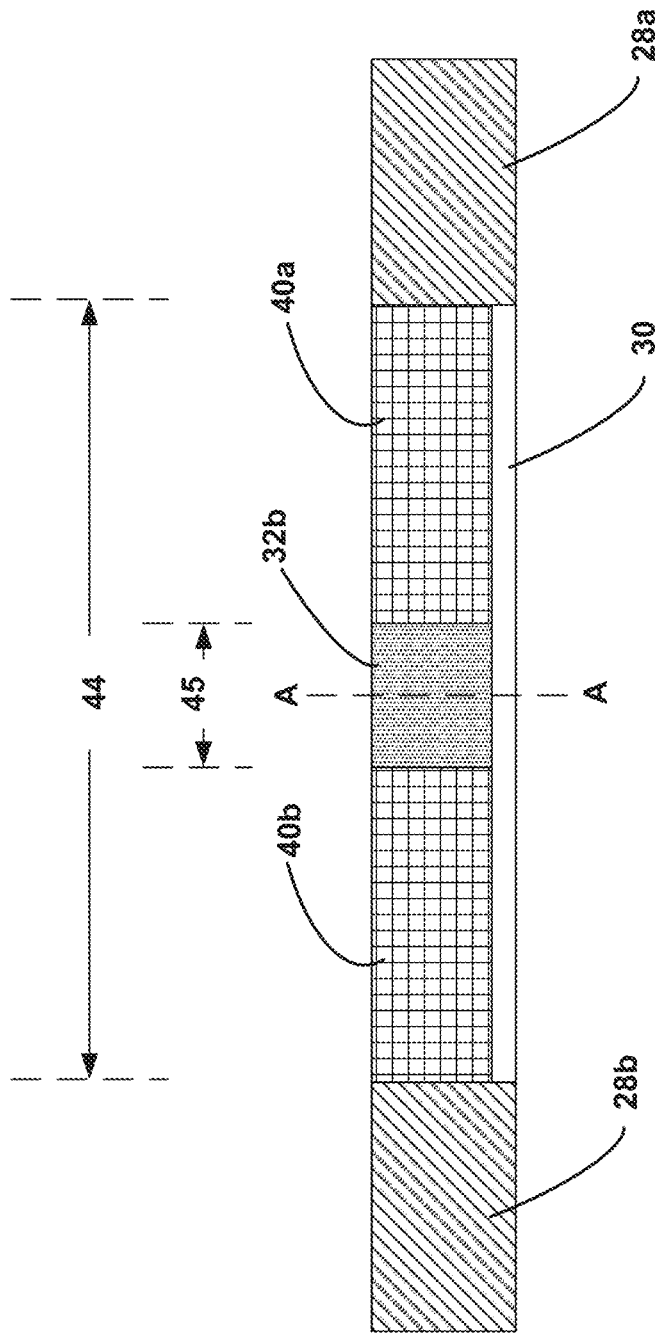
Figure 3C:
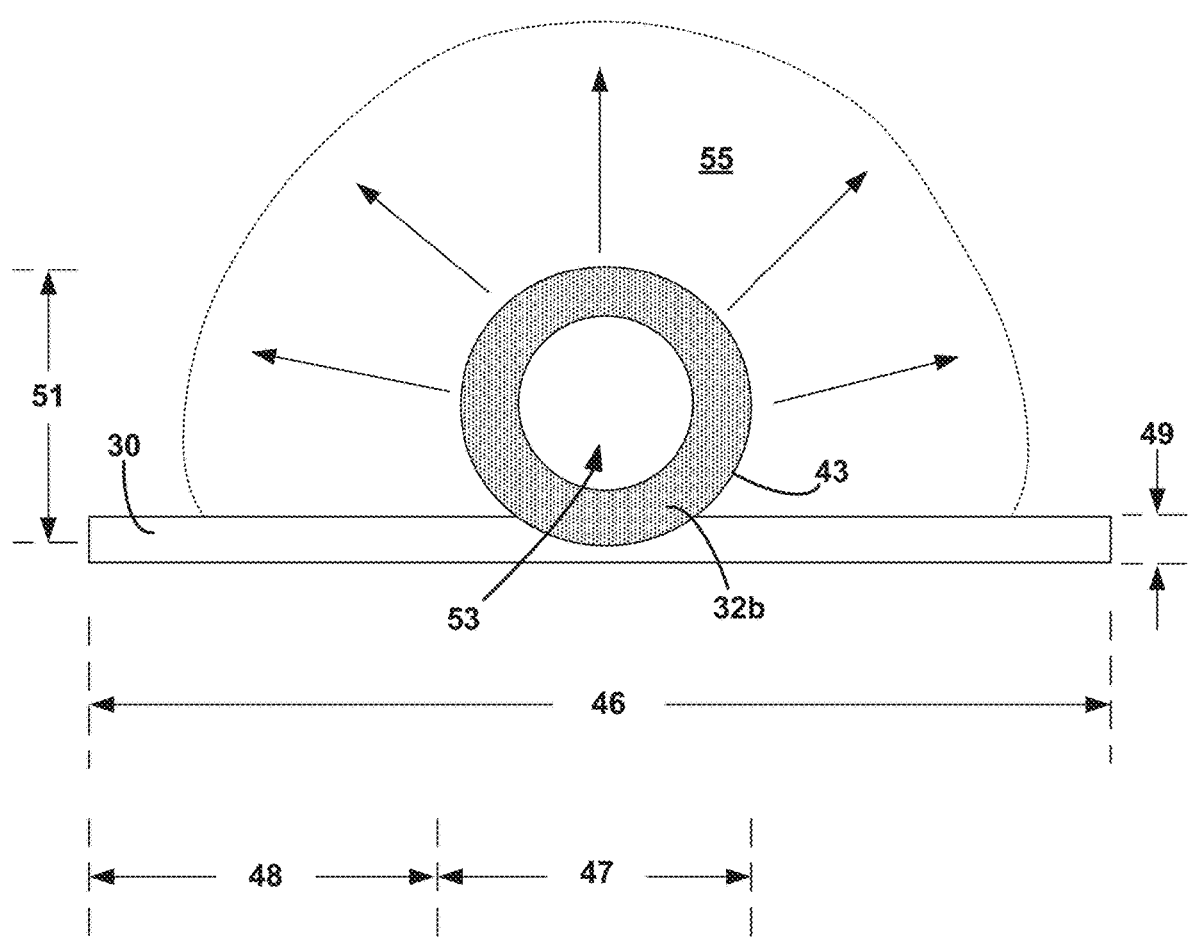

FIGS. 3A-3C are conceptual diagrams illustrating views of shield 30 of implantable medical lead 10. In particular, FIG. 3A illustrates a "top" view in the anterior direction, FIG. 3B illustrates a side view, and FIG. 3C a cross-sectional view taken at line A-A in FIG. 3B.

As illustrated in FIGS. 3A and 3B, shield 30 may extend from a distal end 41a of proximal defibrillation electrode 28a to a proximal end 41b of distal defibrillation electrode 28b in the direction of longitudinal axis "x" of distal portion 16. In some examples, shield 30 may extend over a portion or entirety of one or both of defibrillation electrodes 28. In some examples, shield 30 may not extend to one or both of defibrillation electrodes 28, leaving a gap between the shield and defibrillation electrode.

FIGS. 3A and 3C illustrate shield 30 extending laterally away from pace/sense electrode 32b. As shown in FIG. 3A, shield 30 may be substantially circular in the plane in which the shield extends. In other examples, shield 30 may have other shapes, such as ovoid or rectangular.

A length 44 of shield 30 is greater than a length 45 of pace/sense electrode 32b, such as at least twice the length of pace/sense electrode 32b. A width 46 of shield 30 is greater than a width 47 of pace/sense electrode 32b, such as at least twice width 47 of the pace electrode. In some examples, shield 30 extends a distance 48 beyond pace/sense electrode 32b in the direction of its width, e.g., in a direction orthogonal to its longitudinal axis. In some examples, distance 48 is at least 5 mm, at least 7 mm, or at least 9 mm. One or both of length 44 and width 46 of shield 30 may be at least 15 mm, such as approximately 20 mm. In examples in which shield 30 is circular a dimeter of shield 30 may be at least 15 mm, such as approximately 20 mm.

As illustrated in FIG. 3A, shield 30 includes a plurality of radiopaque markers, including radiopaque marker 42a and radiopaque marker 42b (collectively, "radiopaque markers 42"). Shield 30 may include any number of radiopaque markers or no radiopaque markers. Radiopaque markers 42 may be distributed symmetrically on shield 30, e.g., relative to pace/sense electrode 32b. Radiopaque markers 42 may be positioned on shield 30 to allow a user to visualize at least one of a position or an orientation of the shield within the patient by identification of the radiopaque markers in a fluoroscopic or other image. Radiopaque markers 42 may be different from each other in one or more ways, e.g., size, shape, or orientation, to allow, for example, a physician to differentiate between radiopaque markers 42, in this way facilitating visualization of the orientation of shield 30. For example, one of radiopaque markers 42 positioned on shield 30 may be larger than the rest such that the physician may determine, based on the position of the larger radiopaque marker (e.g., relative to the rest of radiopaque markers 42), the orientation of shield 30.

As illustrated in FIGS. 3A and 3B, distal portion 16 of lead 10 may include lead body portion 40a and lead body portion 40b (collectively, "lead body portions 40"). Lead body portions 40 extend between pace/sense electrode 32b and a respective one of defibrillation electrodes 28. Lead body portions 40 may provide a relatively even or smooth surface transition between the outer profile of pace/sense electrode 32b and the outer profiles of defibrillation electrodes 28. Conductors coupled to electrodes 32b and 28b may extend through lead body portion 40a, and a conductor coupled to electrode 28b may extend through lead body portion 40b. Lead body portions 40a and 40b may formed of one or more polymers, which may be the same as or different from shield 30 and/or other portions of lead body 13.

As illustrated in FIG. 3C, pace/sense electrode 32b may define a lumen 53, e.g., may be in the form of a ring, and a conductor coupled to electrode 28b may extend through lumen 53. Although illustrated in FIG. 3C as a ring, pace/sense electrodes 32 may have other shapes, including partial or segmented ring shapes or arc shapes, in which one or more electrodes or electrode segments extend less than 360-degrees around a circumference of the lead.

Since shield 30 only covers an anterior portion of outer surface 43 of pace/sense electrode 32b, a depth 49 of shield 30 may be less than a depth 51 of pace/sense electrode 32b, such as less than one half of the depth of the electrode. Although illustrated as substantially constant, depth 49 of shield 30 may vary. For example, depth 49 may increase toward pace/sense electrode 32b and/or decrease toward an edge of the shield, e.g., to provide a smooth or otherwise desired transition between shield 30 and pace/sense electrode 32b and/or between shield 30 and tissue of the patient. Additionally, although defibrillation electrodes 28, pace/sense electrode 32b, and lead body portions 40a and 40b are shown in FIG. 3B as having substantially equal depths (e.g., circumferences) that are greater than depth 49 of shield 30, in other examples depth 49 of shield 30 may be similar to that of lead body portions 40a and 40b and pace/sense electrode 32b may extend outward from lead body portions 40a and 40b and shield 30, e.g., due to having a greater depth or being offset from a longitudinal axis defined by lead body portions 40a and 40b.

As illustrated in FIG. 3C, pacing pulses delivered by ICD 9 via pace/sense electrode 32b result in an electrical field 55 proximate the electrode, that "spreads" from electrode outer surface 43. Shield 30 may reduce and/or impede the electrical field in directions from the electrode toward the shield, and allows the spread in directions from the electrode away from the shield. In this manner, shield 30 is configured to make pace/sense electrode 32b directional.

Figure 4:
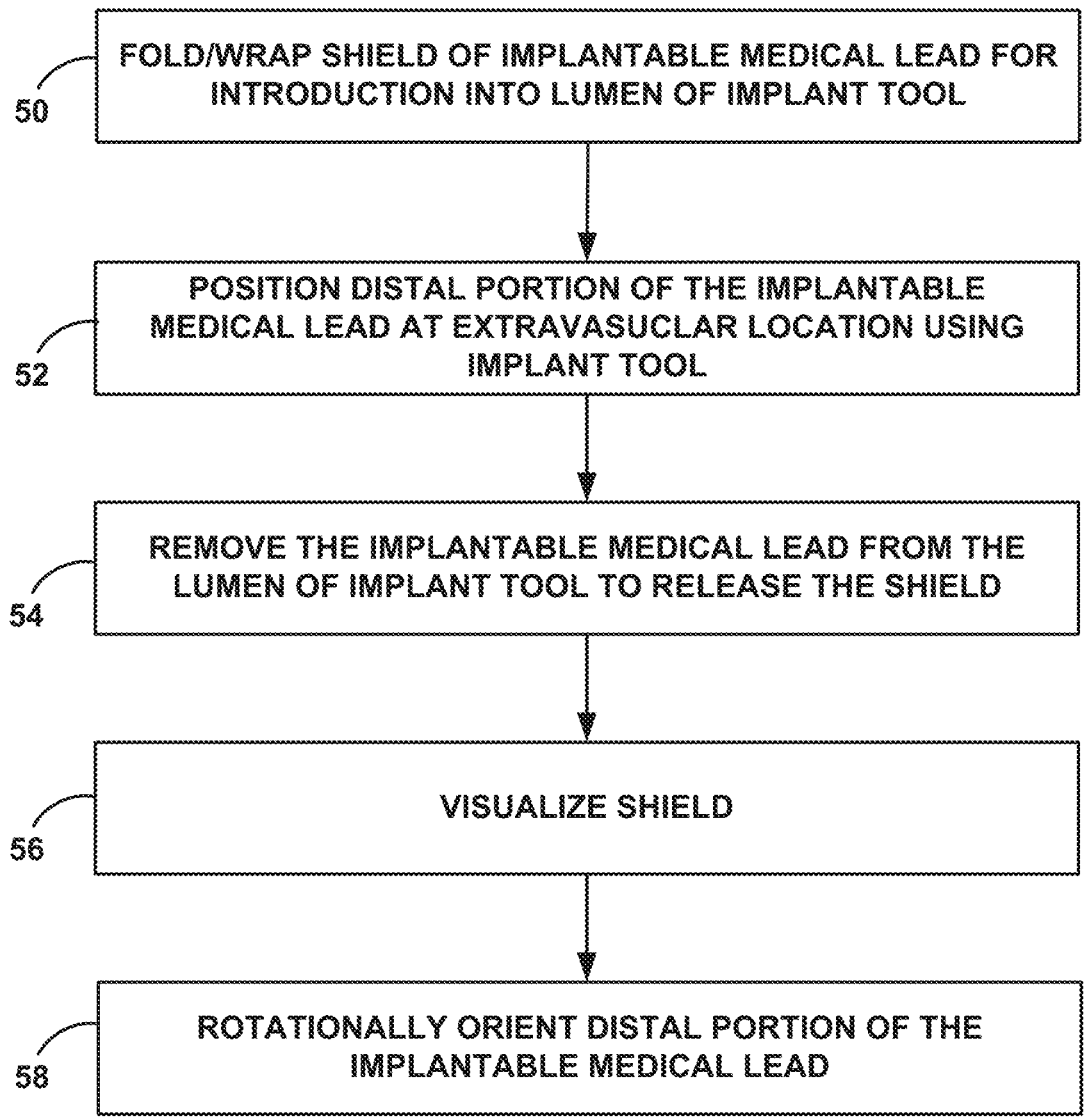
FIG. 4 is a flow diagram illustrating an example technique for implanting an implantable medical lead comprising a shield.

FIG. 4 is a flow diagram illustrating an example technique for implanting an implantable medical lead comprising a shield. FIG. 4 is described with respect to implantable medical lead 10 and shield 30. However, the example technique of FIG. 4 may be used to implant other leads including one or more shields.

A medical practitioner may implant distal portion 16 of implantable medical lead 10 into a substernal or other extravascular location using an implant tool. In some examples, as illustrated by FIG. 4, a medical practitioner or assistant may fold or wrap shield 30 around pace/sense electrode 32b, so that it may fit within a lumen (or a channel) of an implant tool, and introduce distal portion 16 of lead 10 into the lumen (50). In some examples, distal portion 16 may be loaded into the lumen and packaged in a sterile package prior to the implantation procedure, e.g., by a manufacturer of lead 10 and/or the implant tool. The lumen of the implant tool may be cylindrical, or may otherwise have a profile that matches the outer profile of distal portion 16. The undulating configuration of distal portion 16 may be straightened when within the lumen. In one example, the lumen may comprise a sheath. Configurations other than those including a lumen of an implant tool for releasing shield 30 are contemplated by this disclosure.

In some examples, the medical practitioner may introduce the implant tool into the patient via a subxiphoid incision, and advance the implant tool to the extravascular location. Advancement of the tool to the extravascular location may occur before or after lead 10 is loaded into the tool. In either case, distal portion 16 of lead 10 is positioned at the extravascular location using the implant tool, e.g., by advancement through the lumen or advancement of the tool while in the lumen (52). In one embodiment, the implant tool may include a tunneling tool having a rod or other tunneling member and a sheath configured to be placed on the rod.

According to the example of FIG. 4, the medical practitioner removes distal portion 16 of lead 10 from the implant tool to release the shield (54). In the case of an implant tool that includes a sheath with a lumen, the medical practitioner may release the shield by withdrawing the sheath proximally from the patient and/or splitting the sheath. In other embodiments, the implant tool or the sheath of the implant tool may be formed to have a channel or other recessed portion accessible via a longitudinal opening to receive distal portion 16 of lead 10 including shield 30 and the medical practitioner may release the shield by laterally separating distal portion 16 of lead 10 from the channel or other recessed portion of the sheath or implant tool. When shield 30 is free from the lumen, shield 30 may transition from the folded or wrapped configuration to a deployed configuration, e.g., may be elastically deformed to the folded or wrapped configuration and release to the deployed configuration, which may be a relaxed configuration. In some examples, lead 10 may include a fluid, balloon, spring or other actuatable mechanism to transition shield 30 to the deployed configuration.

The medical practitioner may visualize shield 30 within patient, e.g., using fluoroscopy or other medical imaging to identify radiopaque markers (56). The medical practitioner may, if necessary, rotationally orient distal portion 16 of lead 10 so that shield 30 is positioned anteriorly relative to pace/sense electrode 32b (58).

Figure 5:
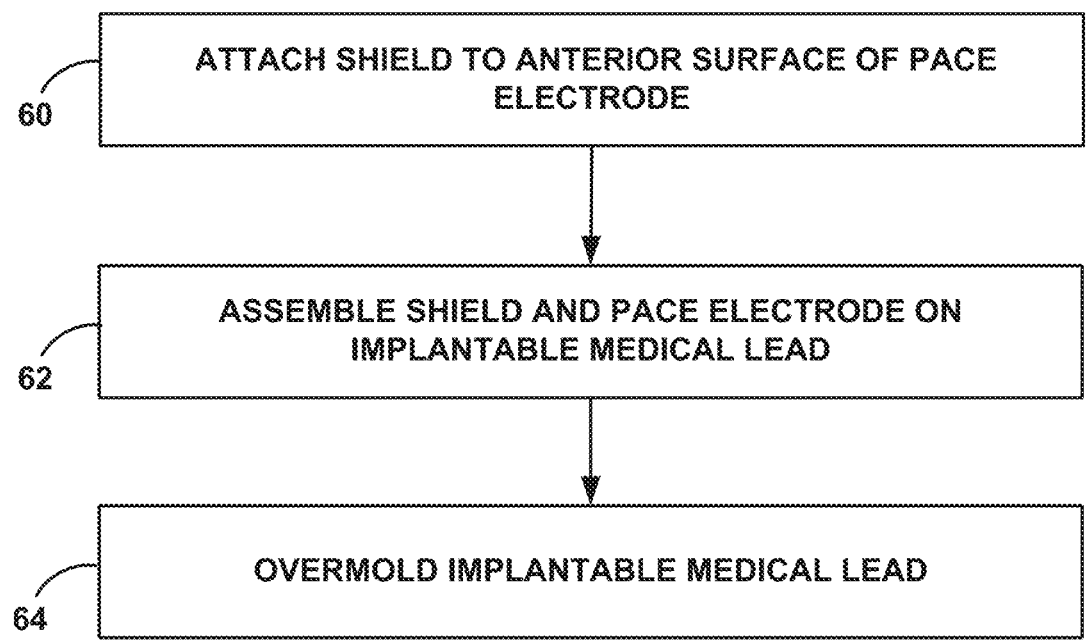
FIG. 5 is a flow diagram illustrating an example technique for manufacturing an implantable medical lead comprising a shield.

FIG. 5 is a flow diagram illustrating an example technique for manufacturing an implantable medical lead comprising a shield. FIG. 5 is described with respect to implantable medical lead 10 and shield 30. However, the example technique of FIG. 5 may be used to implant other leads including one or more shields.

According to the example technique of FIG. 5, shield 30 is attached to an anterior portion of surface 43 of pace/sense electrode 32b (60). In some examples, shield 30 is a separately molded element that is attached to pace/sense electrode 32b using an adhesive. In other examples, shield 30 is molded onto pace/sense electrode 32b. In some examples, the molding of shield 30 onto pace/sense electrode 32b further includes molding lead body portion 40a to a proximal end of pace/sense electrode 32b and lead body portion 40b to a distal end of pace/sense electrode 32b, e.g., shield 30 and lead body portions 40 may be molded as a single piece of a common material. Pace/sense electrode 32b and shield 30 (and in some cases lead body portions 40) may then be assembled onto lead 10 as a unit (62). Lead 10 may then optionally be overmolded (64).

Figure 6:
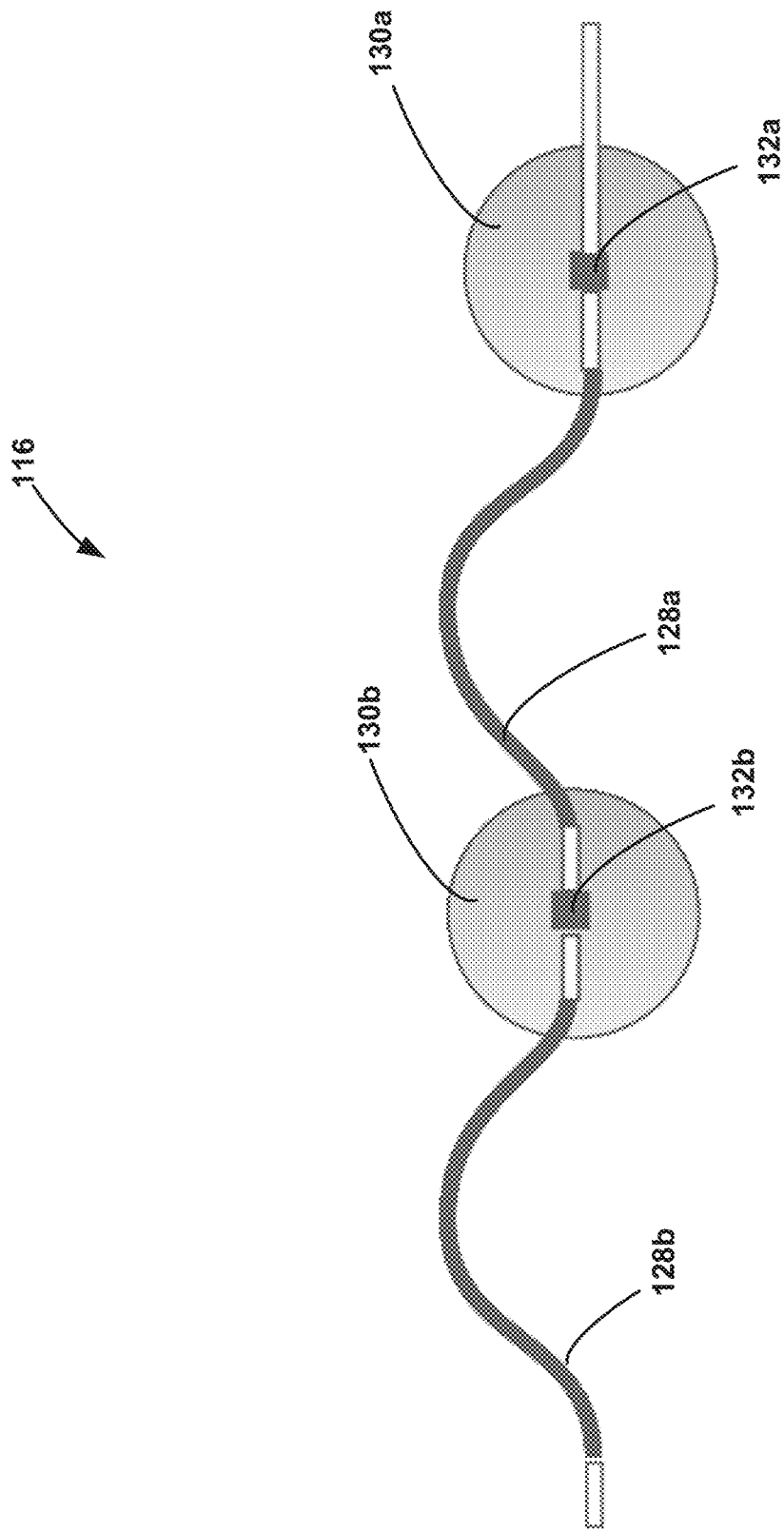
FIG. 6 is a conceptual diagram illustrating a distal portion of an example implantable medical lead comprising a plurality of shields.

FIG. 6 is a conceptual diagram illustrating a distal portion 116 of an example implantable medical lead comprising a plurality of shields. Distal portion 116 is similar to distal portion 16 of lead 10, and like numbered elements of distal portion 116 are similar to those of distal portion 16. For example, distal portion 116 includes defibrillation electrodes 128a and 128b and pace/sense electrodes 132a and 132b, and defines an undulating configuration similar to distal portion 16.

As illustrated in FIG. 6, distal portion 116 includes a first shield 130a over an anterior portion of a surface of pace/sense electrode 132a and a second shield 130b over an anterior portion of a surface of pace/sense electrode 132b. Shield 130a and shield 130b may be the same as or different than each other. In some examples, each of shields 130a and 130b may be the same as or substantially similar to shield 30 described herein with respect to FIGS. 1-5, e.g., may include any combination of one or more of the features described above with respect to shield 30. As shown in FIG. 6, second shield 130b is disposed between defibrillation electrodes 128a and 128b and over a portion of an outer surface of pace/sense electrode 132b. As further shown in FIG. 6, second shield 130b extends laterally away from pace/sense electrode 132b and over at least a portion of defibrillation electrodes 128a and 128b. In the example of FIG. 6, second shield 130b extends over the portions of defibrillation electrodes 128a and 128b comprising ends of defibrillation electrodes 128a and 128b most proximal to pace/sense electrode 132b.

Figure 7:
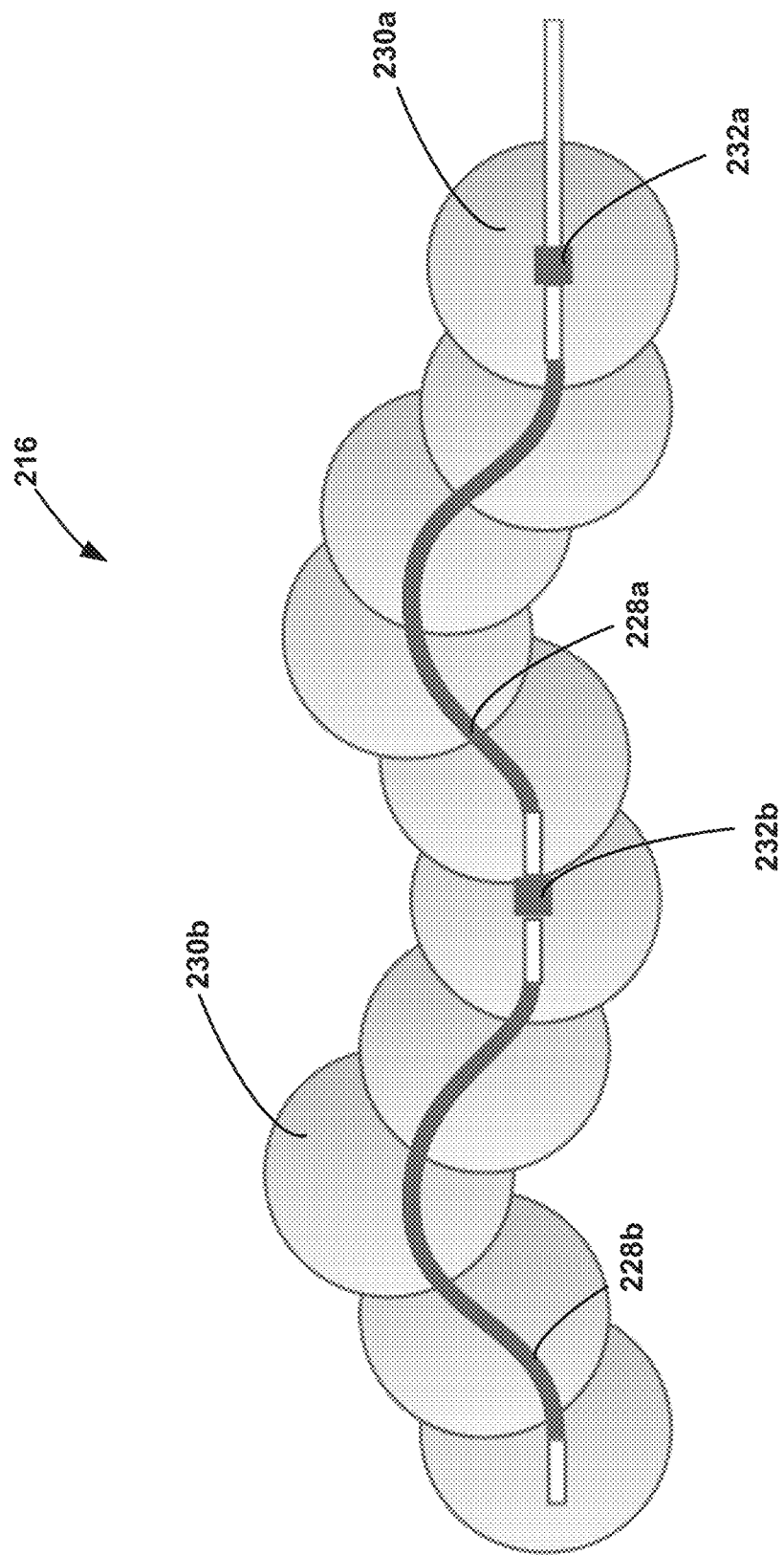
FIG. 7 is a conceptual diagram illustrating a distal portion of another example implantable medical lead comprising a plurality of shields.

FIG. 7 is a conceptual diagram illustrating a distal portion 216 of another example implantable medical lead comprising a plurality of shields. Distal portion 216 is similar to distal portion 16 of lead 10, and like numbered elements of distal portion 216 are similar to those of distal portion 16. For example, distal portion 216 includes defibrillation electrodes 228a and 228b and pace/sense electrodes 232a and 232b, and defines an undulating configuration similar to distal portion 16.

As illustrated in FIG. 7, distal portion 216 includes a plurality of shields including labeled shields 230a and 230b (collectively, "shields 230"). Shields 230 may be the same as or different than each other. In some examples, each of shields 230 may be the same as or substantially similar to shield 30 described herein with respect to FIGS. 1-5, e.g., may include any combination of one or more of the features described above with respect to shield 30.

As illustrated in FIG. 7 shields 230 may collectively cover an anterior portion of an outer surface for each of electrodes 228 and 232. In some examples, defibrillation electrodes 228 may be used to deliver pacing pulses, and shields 230 may provide the same directionality of electrical fields proximate defibrillation electrodes 228 as described with respect to pace sense electrodes 232. Use of a plurality of shields 230 arranged as illustrated in FIG. 7 may provide directionality of electrical fields, while allowing distal portion 216 to be straightened for implantation and then assume the illustrated undulating configuration when implanted.

Figure 8:
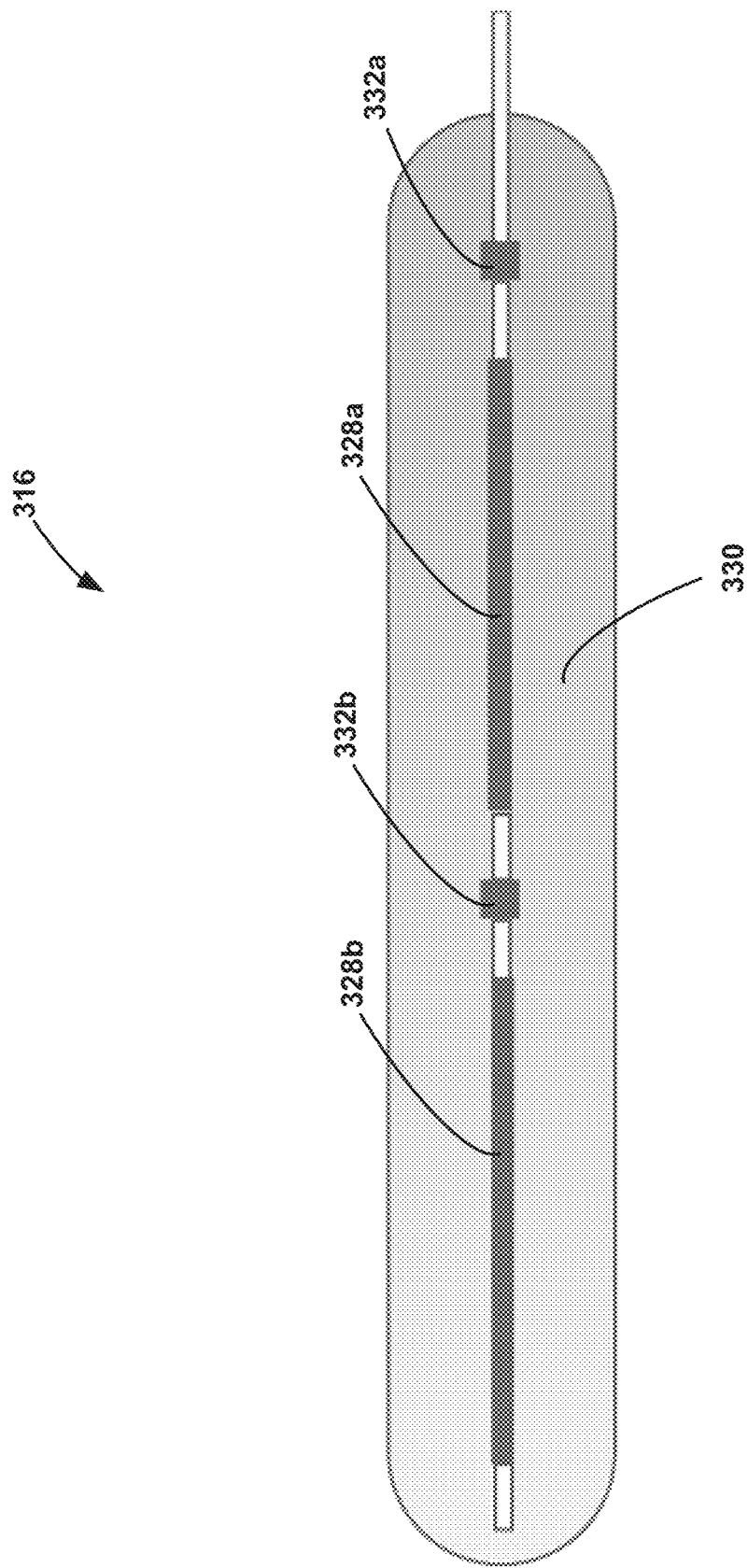
FIG. 8 is a conceptual diagram illustrating a distal portion of another example implantable medical lead comprising a shield.

FIG. 8 is a conceptual diagram illustrating a distal portion 316 of another example implantable medical lead comprising a shield. Like numbered elements of distal portion 316 are similar to those of distal portion 16. For example, distal portion 316 includes defibrillation electrodes 328a and 328b, pace/sense electrodes 332a and 332b. Unlike distal portion 16, however, distal portion 316 defines a straight or substantially straight configuration, rather than an undulating configuration. As illustrated in FIG. 8, distal portion 316 includes a single shield 330 that covers an anterior portion of an outer surface for each of electrodes 228 and 232. Shield 330 may be the same as or substantially similar to shield 30 described herein with respect to FIGS. 1-5, e.g., may include any combination of one or more of the features described above with respect to shield 30.

Although the example implantable medical lead distal portions illustrated herein have generally included two defibrillation electrodes and two pace/sense electrodes, with one of the pace/sense electrodes between the defibrillation electrodes and the other of the pace/sense electrodes proximal of the defibrillation electrodes, any the shields described herein may be included as part of differently configured implantable medical leads. For example, some implantable medical leads may include a single defibrillation electrode and one or more pace/sense electrodes located distal and/or proximal of the defibrillation electrode. In other examples, an implantable medical lead that includes one or more stimulation electrodes, not necessarily for cardiac pacing, does not include a defibrillation electrode. In any such examples, one or more shields configured as described herein may be located over a portion of a surface of one or more electrodes.

Figure 9:
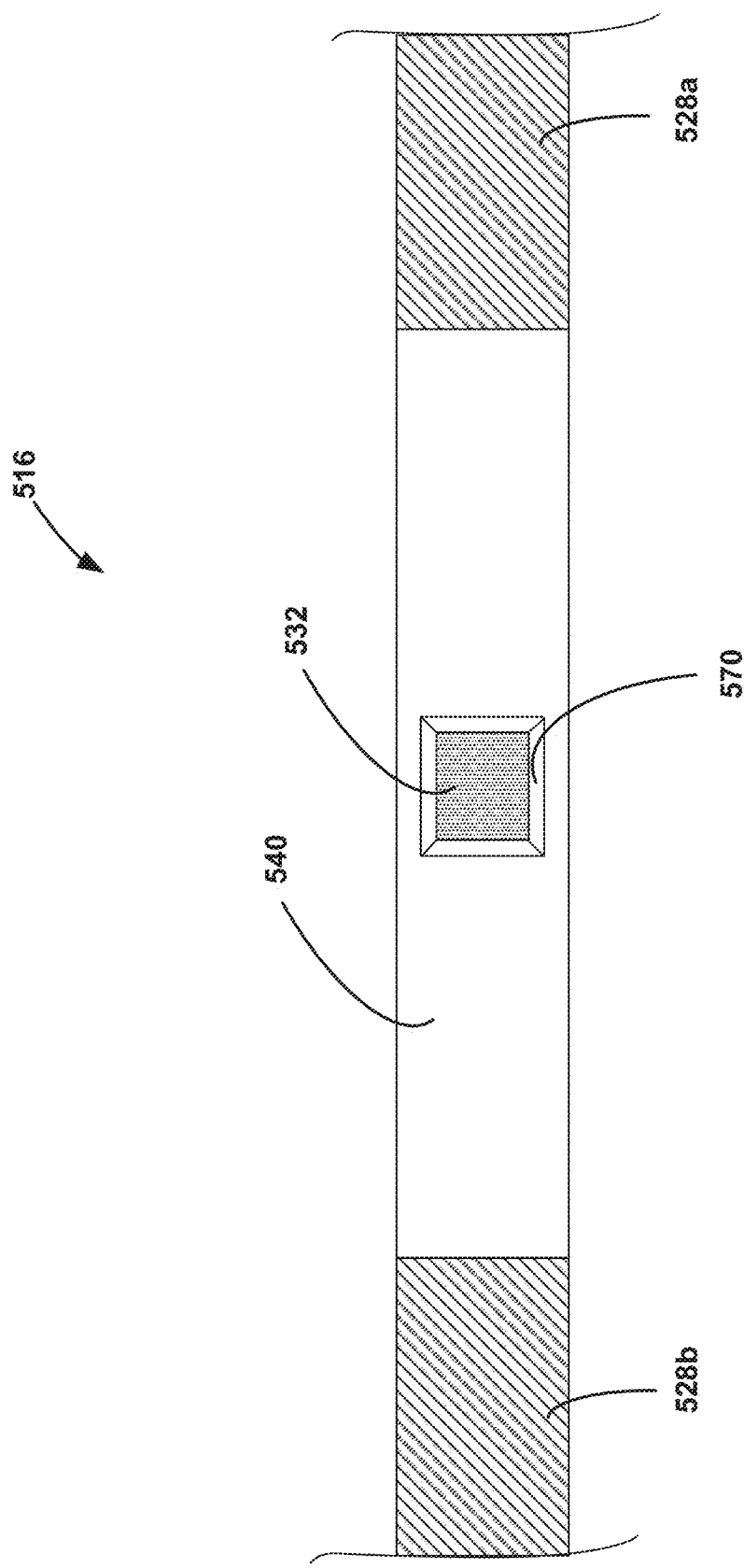
FIG. 9 is a conceptual diagram illustrating part of a distal portion of another implantable medical lead comprising a shield.

FIG. 9 is a conceptual diagram illustrating part of a distal portion 516 of another implantable medical lead comprising a shield. Distal portion 516 may be similar to distal portion 16 of lead 10, and like numbered elements of distal portion 516 may be similar to those of distal portion 16. For example, distal portion 516 includes defibrillation electrodes 528a and 528b (collectively, "defibrillation electrodes 528") and pace/sense electrode 532.

Distal portion 516 also includes a lead body portion 540 extending from defibrillation electrode 528a to defibrillation electrode 528b. Lead body portion 540 may provide a relatively even or smooth surface transition between the outer profiles of defibrillation electrodes 528. Lead body portion 540 may be formed of an insulative material and conductors coupled to electrodes 532 and 528b may extend through lead body portion 540.

In the example illustrated by FIG. 9, pace/sense electrode 532 is located within a recessed portion 570 of lead body portion 540. Lead body portion 540 having recessed portion 570 may cover an anterior portion of a surface of pace/sense electrode 532 and impede an electrical field in at least an anterior direction. Although not illustrated in FIG. 9, distal portion 516 may further include a shield 30 or any other shield as described herein over the anterior portion of the surface of pace/sense electrode 532 to impede the electrical field in the anterior direction.

Figure 10:
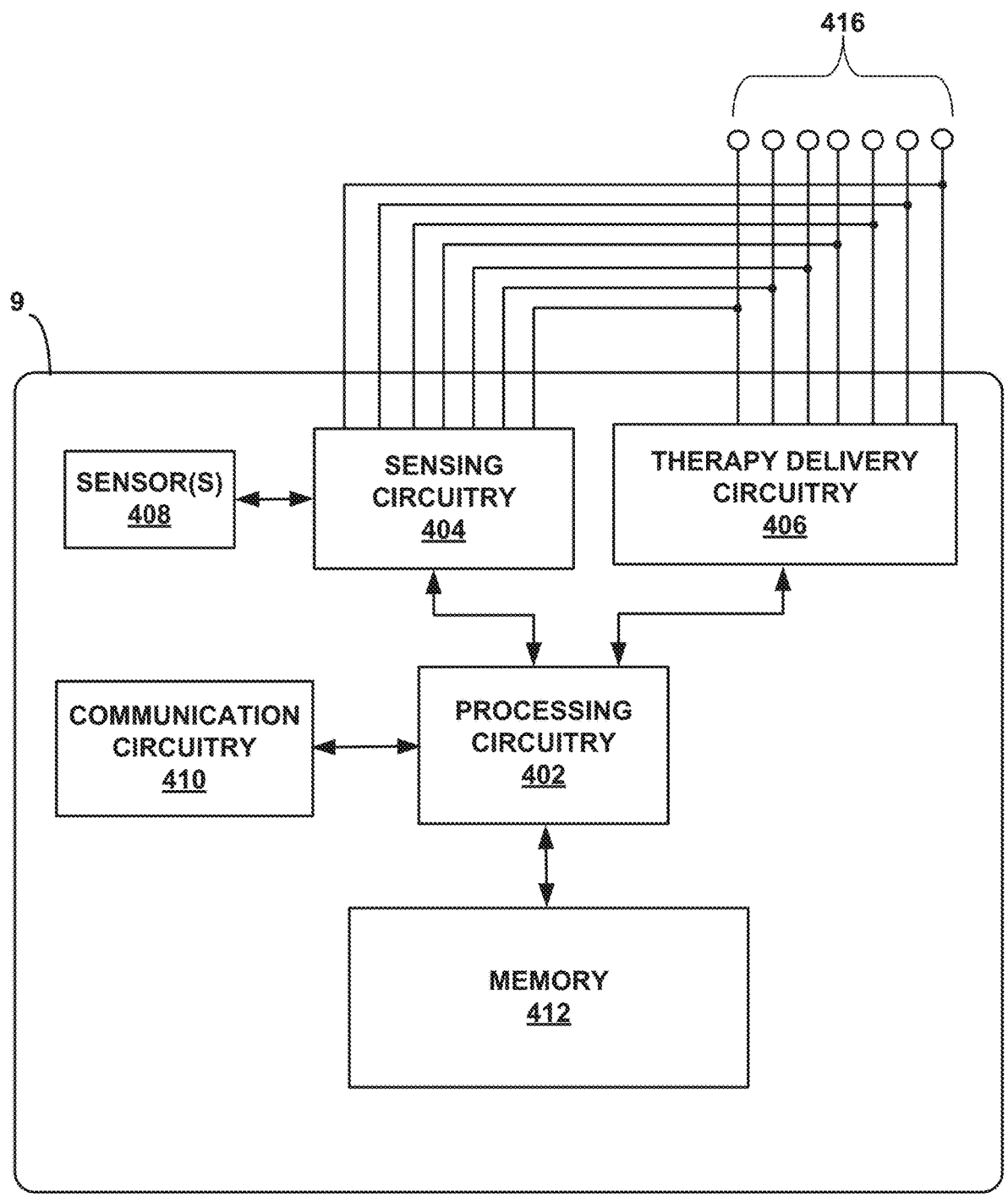
FIG. 10 is a functional block diagram of an example configuration of electronic components of an example ICD.

FIG. 10 is a functional block diagram of an example configuration of electronic components and other components of ICD 9. ICD 9 includes a processing circuitry 402, sensing circuitry 404, therapy delivery circuitry 406, sensors 408, communication circuitry 410, and memory 412. In other examples, ICD 9 may include more or fewer components. The described circuitry and other components may be implemented together on a common hardware component or separately as discrete but interoperable hardware or software components. Depiction of different features is intended to highlight different functional aspects and does not necessarily imply that such circuitry and other components must be realized by separate hardware or software components. Rather, functionality associated with one or more circuitries and components may be performed by separate hardware or software components, or integrated within common or separate hardware or software components.

Sensing circuitry 404 may be electrically coupled to some or all of electrodes 416, which may correspond to any of the defibrillation, pace/sense, and housing electrodes described herein. Sensing circuitry 404 is configured to obtain signals sensed via one or more combinations of electrodes 416 and process the obtained signals.

The components of sensing circuitry 404 may be analog components, digital components or a combination thereof. Sensing circuitry 404 may, for example, include one or more sense amplifiers, filters, rectifiers, threshold detectors, analog-to-digital converters (ADCs) or the like. Sensing circuitry 404 may convert the sensed signals to digital form and provide the digital signals to processing circuitry 402 for processing or analysis. For example, sensing circuitry 404 may amplify signals from the sensing electrodes and convert the amplified signals to multi-bit digital signals by an ADC. Sensing circuitry 404 may also compare processed signals to a threshold to detect the existence of atrial or ventricular depolarizations (e.g., P- or R waves) and indicate the existence of the atrial depolarization (e.g., P-waves) or ventricular depolarizations (e.g., R-waves) to processing circuitry 402. As shown in FIG. 10, ICD 9 may additionally include one or more sensors 408, such as one or more accelerometers, which may be configured to provide signals indicative of other parameters of a patient, such as activity or posture, to processing circuitry 402.

Processing circuitry 402 may process the signals from sensing circuitry 404 to monitor electrical activity of heart 26 of patient 12. Processing circuitry 402 may store signals obtained by sensing circuitry 404 as well as any generated EGM waveforms, marker channel data or other data derived based on the sensed signals in memory 412. Processing circuitry 402 may analyze the EGM waveforms and/or marker channel data to detect arrhythmias (e.g., bradycardia or tachycardia). In response to detecting the cardiac event, processing circuitry 402 may control therapy delivery circuitry 406 to deliver the desired therapy to treat the cardiac event, e.g., defibrillation shock, cardioversion shock, ATP, post shock pacing, or bradycardia pacing.

Therapy delivery circuitry 406 is configured to generate and deliver electrical therapy to heart 26. Therapy delivery circuitry 406 may include one or more pulse generators, capacitors, and/or other components capable of generating and/or storing energy to deliver as pacing therapy, defibrillation therapy, cardioversion therapy, cardiac resynchronization therapy, other therapy or a combination of therapies. In some instances, therapy delivery circuitry 406 may include a first set of components configured to provide pacing therapy and a second set of components configured to provide defibrillation therapy. In other instances, therapy delivery circuitry 406 may utilize the same set of components to provide both pacing and defibrillation therapy. In still other instances, therapy delivery circuitry 406 may share some of the defibrillation and pacing therapy components while using other components solely for defibrillation or pacing. Processing circuitry 402 may control therapy delivery circuitry 406 to deliver the generated therapy to heart 26 via one or more combinations of electrodes 416. Although not shown in FIG. 10, ICD 9 may include switching circuitry configurable by processing circuitry 402 to control which of electrodes 416 is connected to therapy delivery circuitry 406 and sensing circuitry 404.

Communication circuitry 410 includes any suitable hardware, firmware, software or any combination thereof for communicating with another device, such as a clinician programmer, a patient monitoring device, or the like. For example, communication circuitry 410 may include appropriate modulation, demodulation, frequency conversion, filtering, and amplifier components for transmission and reception of data with the aid of an antenna.

The various components of ICD 9 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Processing circuitry 402 may include fixed function circuitry and/or programmable processing circuitry. The functions attributed to processing circuitry 402 herein may be embodied as software, firmware, hardware or any combination thereof.

Memory 412 may include computer-readable instructions that, when executed by processing circuitry 402 or other components of ICD 9, cause one or more components of ICD 9 to perform various functions attributed to those components in this disclosure. Memory 412 may include any volatile, non-volatile, magnetic, optical, or electrical media, such as a random-access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

The leads and systems described herein may be used at least partially within the substernal space, e.g., within anterior mediastinum of patient, to provide an extravascular ICD system. An implanter (e.g., physician) may implant the distal portion of the lead intra-thoracically using any of a number of implant tools, e.g., tunneling rod, sheath, or other tool that can traverse the diagrammatic attachments and form a tunnel in the substernal location. For example, the implanter may create an incision near the center of the torso of the patient, e.g., and introduce the implant tool into the substernal location via the incision. The implant tool is advanced from the incision superior along the posterior of the sternum in the substernal location. The distal portion of the lead is introduced into the tunnel via implant tool (e.g., via a sheath). As the distal portion is advanced through the substernal tunnel, the distal portion is relatively straight. The pre-formed or shaped undulating configuration is flexible enough to be straightened out while routing the lead through a sheath or other lumen or channel of the implant tool. Once the distal portion is in place, the implant tool is withdrawn toward the incision and removed from the body of the patient while leaving the lead in place along the substernal path. As the implant tool is withdrawn, the distal end of the lead takes on its pre-formed undulating configuration, and the shield transitions to its deployed configuration.

In some examples, rather than extending in a superior direction along the sternum, the distal portion of the lead may be oriented orthogonal or otherwise transverse to the sternum and/or inferior to the heart. In such examples, the lead may include one or more shields that cover a portion of an outer surface of one or more electrodes, e.g., an anterior and/or inferior portion, according to any of the examples described herein. Such shield(s) may impede an electrical field in a direction away from the heart, which may be an anterior and/or inferior direction.

In this way, various aspects of the techniques may enable the following clauses.

Clause 1: An implantable medical lead includes a first defibrillation electrode and a second defibrillation electrode, the first and second defibrillation electrodes configured to deliver antitachyarrhythmia shocks; a pace electrode disposed between the first defibrillation electrode and the second defibrillation electrode, the pace electrode configured to deliver a pacing pulse that generates an electric field proximate to the pace electrode; and a shield disposed between the first defibrillation electrode and the second defibrillation electrode, over a portion of an outer surface of the pace electrode, and extending laterally away from the pace electrode, wherein the shield is configured to impede the electric field in a direction from the pace electrode away from a heart.

Clause 2: The implantable medical lead of clause 1, wherein a length of the shield is greater than a length of the pace electrode.

Clause 3: The implantable medical lead of clause 2, wherein the length of the shield is at least twice the length of the pace electrode.

Clause 4: The implantable medical lead of any of clauses 1-3, wherein the shield extends from a distal end of a proximal one of the first defibrillation electrode and the second defibrillation electrode to a proximal end of a distal one of the first defibrillation electrode and the second defibrillation electrode.

Clause 5: The implantable medical lead of any of clauses 1-4, wherein a width of the shield is greater than a width of the pace electrode.

Clause 6: The implantable medical lead of clause 5, wherein the width of the shield is at least twice the width of the pace electrode.

Clause 7: The implantable medical lead of any of clauses 1-6, wherein the shield extends at least 5 millimeters beyond the pace electrode in each direction orthogonal to a longitudinal axis of the pace electrode.

Clause 8: The implantable medical lead of any of clauses 1-7, wherein the shield is symmetrical about a longitudinal axis of the pace electrode.

Clause 9: The implantable medical lead of any of clauses 1-8, wherein a diameter of the shield is greater than 15 millimeters.

Clause 10: The implantable medical lead of clause 9, wherein the diameter of the shield is approximately 20 millimeters.

Clause 11: The implantable medical lead of any of clauses 1-10, wherein the shield is electrically insulative.

Clause 12: The implantable medical lead of any of clauses 1-11, wherein the shield includes a polymer.

Clause 13: The implantable medical lead of any of clauses 1-12, wherein the shield includes polyurethane.

Clause 14: The implantable medical lead of any of clauses 1-13, wherein the shield is configured to be folded or wrapped around the pace electrode for delivery via a lumen of an implant tool, and configured to elastically unfold or unwrap to an open configuration when released from the lumen.

Clause 15: The implantable medical lead of any of clauses 1-14, wherein the shield includes at least one radiopaque marker spaced laterally from the pace electrode.

Clause 16: The implantable medical lead of clause 15, wherein the shield includes a plurality of radiopaque markers distributed symmetrically relative to the pace electrode.

Clause 17: The implantable medical lead of any of clauses 1-16, wherein the distal portion of the implantable medical lead defines an undulating configuration including a first peak extending in a first direction, a second peak extending in the first direction, and a third peak, between the first peak and the second peak, extending in a second direction opposite the first direction, and wherein at least a portion of the first defibrillation electrode is disposed on the first peak, at least a portion of the second defibrillation electrode is disposed on the second peak, and at least a portion of the pace electrode is disposed on the third peak.

Clause 18: The implantable medical lead of clause 17, wherein the undulating configuration defines a substantially sinusoidal configuration.

Clause 19: The implantable medical lead of any of clauses 1-18, wherein the shield is planar.

Clause 20: The implantable medical lead of any of clauses 1-18, wherein the shield is nonplanar.

Clause 21: The implantable medical lead of clause 20, wherein a portion of the shield spaced further away laterally from the pace electrode is positioned more posteriorly than a portion closer to the pace electrode.

Clause 22: The implantable medical lead of any of clauses 1-21, wherein the shield includes at least one support structure configured to facilitate at least one of deployment or articulation of the shield.

Clause 23: The implantable medical lead of clause 22, wherein the support structure includes Nitinol.

Clause 24: The implantable medical lead of clause 22 or 23, wherein the support structure is located on a periphery of the shield.

Clause 25: The implantable medical lead of any of clauses 1-24, further including a lead body portion including a recess, wherein the pace electrode is recessed within the recess of the lead body portion.

Clause 26: The implantable medical lead of any of clauses 1-25, wherein the pace electrode includes a first pace electrode and the shield includes a first shield, the implantable medical lead includes a second pace electrode; and a second shield disposed over a portion of an outer surface of the second pace electrode, and extending laterally away from the second pace electrode, wherein the second shield is configured to impede the electric field in a direction from the second pace electrode away from the heart.

Clause 27: The implantable medical lead of any of clauses 1-26, further including a plurality of shields distributed along a length of the distal portion of the implantable medical lead.

Clause 28: The implantable medical lead of any of clauses 1-27, wherein the portion of the surface of the pace electrode is an anterior portion, and the shield is configured to impede the electric field in an anterior direction from the pace electrode.

Clause 29: The implantable medical lead of any of clauses 1-27, wherein the portion of the surface of the pace electrode is an inferior portion, and the shield is configured to impede the electric field in an inferior direction from the pace electrode.

Clause 30: An implantable cardioverter-defibrillator (ICD) system includes the implantable medical lead of any of claims 1-29; and an ICD configured to generate the pacing pulse.

Clause 31: A method of implanting the implantable medical lead of any of clauses 1-29 includes positioning the distal portion the implantable medical lead at a location within the patient; and rotationally orienting the distal portion of implantable medical lead such that the shield is opposite the heart relative to the pace electrode.

Clause 32: The method of clause 31, further including visually identifying a plurality of radiopaque markers of the shield to visualize at least one of a position or an orientation of the shield within the patient.

Clause 33: The method of clause 31 or 32, further including removing the implantable medical lead from a lumen of an implant tool to release the shield from a wrapped or folded configuration to an open configuration.

Clause 34: The method of any of clauses 31-33, wherein rotationality orienting the distal portion includes rotationally orienting the distal portion such that the shield is positioned anteriorly relative to the pace electrode.

Clause 35: The method of any of clauses 31-33, wherein rotationality orienting the distal portion includes rotationally orienting the distal portion such that the shield is positioned inferiorly relative to the pace electrode.

Clause 36: A method of manufacturing the implantable medical lead of any of clauses 1-29 includes attaching the shield to the surface of the pace electrode; and subsequently assembling the shield and the pace electrode on the implantable medical lead.

Clause 37: The method of clause 36, wherein attaching the shield to the surface of the pace electrode includes molding the shield onto the pace electrode.

Clause 38: The method of clause 37, wherein molding the shield onto the pace electrode further includes molding a first lead body portion onto a distal end of the pace electrode and a second lead body portion onto a proximal end of the pace electrode.

It will be appreciated by persons skilled in the art that the present application is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the application, which is limited only by the following claims.

What is claimed is:

1. An implantable medical lead comprising:
   a first defibrillation electrode and a second defibrillation electrode, the first and second defibrillation electrodes configured to deliver anti-tachyarrhythmia shocks;
   a pace electrode disposed between the first defibrillation electrode and the second defibrillation electrode, the pace electrode configured to deliver a pacing pulse that generates an electric field proximate to the pace electrode; and
   a shield,
      wherein the shield is disposed over a portion of an outer surface of the pace electrode,
      wherein the shield extends laterally away from the pace electrode in a deployed configuration,
      wherein the shield is configured to impede the electric field in a direction from the pace electrode away from a heart in the deployed configuration,
      wherein the shield is disposed between the first defibrillation electrode and the second defibrillation electrode, and
      wherein the shield extends:
         over only a portion of the first defibrillation electrode, wherein the portion of the first defibrillation electrode comprises an end of the first defibrillation electrode most proximal to the pace electrode, and over only a portion of the second defibrillation electrode, wherein the portion of the second defibrillation electrode comprises an end of the second defibrillation electrode most proximal to the pace electrode.

2. The implantable medical lead of claim 1, wherein a length of the shield is greater than a length of the pace electrode.

3. The implantable medical lead of claim 1, wherein a width of the shield is greater than a width of the pace electrode in the deployed configuration.

4. The implantable medical lead of claim 1, wherein the shield is electrically insulative.

5. The implantable medical lead of claim 1, wherein the shield is configured to be folded or wrapped around the pace electrode for delivery via a lumen of an implant tool, and configured to elastically unfold or unwrap to the deployed configuration when released from the lumen.

6. The implantable medical lead of claim 1,
wherein a distal portion of the implantable medical lead defines an undulating configuration including a first peak extending in a first direction, a second peak extending in the first direction, and a third peak, between the first peak and the second peak, extending in a second direction opposite the first direction, and
wherein at least a portion of the first defibrillation electrode is disposed on the first peak, at least a portion of the second defibrillation electrode is disposed on the second peak, and at least a portion of the pace electrode is disposed on the third peak.

7. The implantable medical lead of claim 1, wherein the shield comprises at least one support structure configured to facilitate transitioning the shield to the deployed configuration.

8. The implantable medical lead of claim 7, wherein the support structure comprises Nitinol.

9. The implantable medical lead of claim 1, further comprising a lead body portion comprising a recess, wherein the pace electrode is recessed within the recess of the lead body portion.

10. The implantable medical lead of claim 1, wherein the pace electrode comprises a first pace electrode and the shield comprises a first shield and the deployed configuration of the first shield comprises a first deployed configuration, the implantable medical lead comprising:
a second pace electrode; and
a second shield disposed over a portion of an outer surface of the second pace electrode, and extending laterally away from the second pace electrode in a second deployed configuration, wherein the second shield is configured to impede the electric field in a direction from the second pace electrode away from the heart in the second deployed configuration.

11. The implantable medical lead of claim 1, further comprising a plurality of shields distributed along a length of a distal portion of the implantable medical lead.

12. The implantable medical lead of claim 1, wherein the shield is configured to impede the electric field in a direction from the portion of the surface of the pace electrode to the shield.

13. The implantable medical lead of claim 1, wherein the portion of the surface of the pace electrode is an inferior portion, and the shield is configured to impede the electric field in an inferior direction from the pace electrode.

14. The implantable medical lead of claim 1, further comprising a balloon configured to actuate transitioning the shield to the deployed configuration.

15. An implantable medical system comprising:
an implantable medical device comprising:
a housing; and
therapy delivery circuitry within the housing and configured to generate anti-tachyarrhythmia shocks and a pacing pulse; and
an implantable medical lead configured to be coupled to the medical device comprising:
a first defibrillation electrode and a second defibrillation electrode, the first and second defibrillation electrodes configured to deliver the anti-tachyarrhythmia shocks;
a pace electrode disposed between the first defibrillation electrode and the second defibrillation electrode, the pace electrode configured to deliver the pacing pulse, wherein the pacing pulse generates an electric field proximate to the pace electrode; and
a shield,
wherein the shield is disposed over a portion of an outer surface of the pace electrode,
wherein the shield extends laterally away from the pace electrode in a deployed configuration,
wherein the shield is configured to impede the electric field in a direction from the pace electrode away from a heart in the deployed configuration,
wherein the shield is disposed between the first defibrillation electrode and the second defibrillation electrode, and
wherein the shield extends:
over only a portion of the first defibrillation electrode, wherein the portion of the first defibrillation electrode comprises an end of the first defibrillation electrode most proximal to the pace electrode, and
over only a portion of the second defibrillation electrode, wherein the portion of the second defibrillation electrode comprises an end of the second defibrillation electrode most proximal to the pace electrode;
and
an ICD configured to generate the pacing pulse.

16. The implantable medical system of claim 15, further comprising a balloon configured to actuate transitioning the shield to the deployed configuration.

17. A method of implanting an implantable medical lead, the method comprising:
positioning a distal portion of an implantable medical lead at a location within a patient, wherein the implantable medical lead comprises:
a first defibrillation electrode and a second defibrillation electrode, the first and second defibrillation electrodes configured to deliver anti-tachyarrhythmia shocks;
a pace electrode disposed between the first defibrillation electrode and the second defibrillation electrode, the pace electrode configured to deliver a pacing pulse that generates an electric field proximate to the pace electrode; and
a shield,
wherein the shield is disposed over a portion of an outer surface of the pace electrode,
wherein the shield extends laterally away from the pace electrode in a deployed configuration, wherein the shield is disposed between the first defibrillation electrode and the second defibrillation electrode, wherein the shield extends:
over only a portion of the first defibrillation electrode, wherein the portion of the first defibrillation electrode comprises an end of the first defibrillation electrode most proximal to the pace electrode, and over only a portion of the second defibrillation electrode, wherein the portion of the second defibrillation electrode comprises an end of the second defibrillation electrode most proximal to the pace electrode, and wherein the shield is configured to impede the electric field in a direction from the pace electrode away from a heart in the deployed configuration; and rotationally orienting the distal portion of implantable medical lead such that the shield is opposite the heart relative to the pace electrode.

18. The method of claim 17, further comprising removing the implantable medical lead from a lumen of an implant tool to release the shield from a wrapped or folded configuration to the deployed configuration.

19. The method of claim 17, further comprising actuating a transition of the shield to the deployed configuration with a balloon.

* * * * *